US012331337B2

(12) United States Patent
Lee et al.

(10) Patent No.: US 12,331,337 B2
(45) Date of Patent: Jun. 17, 2025

(54) **Fe-S FUSION PROTEIN ACTING AS ELECTRON TRANSFER CHAIN, CARBON MONOXIDE FORMATE REDOX ENZYME MEDIATED THROUGH FES FUSION PROTEIN, STRAIN BCF12 DERIVED FROM *THERMOCOCCUS* WHEREIN ENZYME IS TRANSFORMED, AND USE THEREOF**

(71) Applicant: KOREA INSTITUTE OF OCEAN SCIENCE & TECHNOLOGY, Busan (KR)

(72) Inventors: Jung-Hyun Lee, Busan (KR); Jae Kyu Lim, Busan (KR); Hyun Sook Lee, Busan (KR); Sung Gyun Kang, Busan (KR); Kae Kyoung Kwon, Busan (KR); Yun Jae Kim, Busan (KR); Ji-In Yang, Busan (KR)

(73) Assignee: KOREA INSTITUTE OF OCEAN SCIENCE & TECHNOLOGY, Busan (KR)

( * ) Notice: Subject to any disclaimer, the term of this patent is extended or adjusted under 35 U.S.C. 154(b) by 1003 days.

(21) Appl. No.: 17/292,967

(22) PCT Filed: Nov. 28, 2018

(86) PCT No.: PCT/KR2018/014807
§ 371 (c)(1),
(2) Date: May 11, 2021

(87) PCT Pub. No.: WO2020/101100
PCT Pub. Date: May 22, 2020

(65) Prior Publication Data
US 2022/0213463 A1 Jul. 7, 2022

(30) Foreign Application Priority Data

Nov. 12, 2018 (KR) .................. 10-2018-0138462
Nov. 12, 2018 (KR) .................. 10-2018-0138467
Nov. 12, 2018 (KR) .................. 10-2018-0138475

(51) Int. Cl.
*C12N 9/96* (2006.01)
*C12N 9/02* (2006.01)
*C12N 15/52* (2006.01)
*C12P 7/40* (2006.01)

(52) U.S. Cl.
CPC ............ *C12N 9/96* (2013.01); *C12N 9/0008* (2013.01); *C12N 15/52* (2013.01); *C12P 7/40* (2013.01); *C12Y 102/01002* (2013.01); *C12Y 102/02001* (2013.01); *C12Y 102/07004* (2013.01)

(58) Field of Classification Search
None
See application file for complete search history.

(56) References Cited

FOREIGN PATENT DOCUMENTS

| JP | 4760951 B2 | 8/2011 |
|---|---|---|
| KR | 10-2014-0064469 A | 5/2014 |
| KR | 10-2016-0040088 A | 4/2016 |
| KR | 10-2017-0024466 A | 3/2017 |
| KR | 10-2018-0005712 A | 1/2018 |

OTHER PUBLICATIONS

Accession P31896. Jul. 1, 1993 (Year: 1993).*
Accession AAB00156. Sep. 21, 2000. (Year: 2000).*
Accession B6YWP3. Jan. 20, 2009. (Year: 2009).*
International Search Report for PCT/KR2018/014807 mailed on Aug. 9, 2019.
Hoff, K.G. et al. "In vivo fluorescent detection of Fe-S clusters coordinated by human GRX2", Chemistry & Biology. 2009, vol. 16, pp. 1299-1308.
Mazumder, T. K. et al. "Carbon monoxide conversion to formate by methanosarcina barkeri", Biotechnology Letters. 1985, vol. 7, No. 6, pp. 377-382.
Lee, H. S. et al. "The complete genome sequence of Thermococcus onnurineus NA1 reveals a mixed heterotrophic and carboxydotrophic metabolism", Journal of Bacteriology. 2008, vol. 190, No. 22, pp. 7491-7499.
Joseph Sambrook et al., Molecular Cloning, A Laboratory Manual, Cold Spring Harbor Laboratory Press (2001).
Toon H. Evers et al., "Quantitative Understanding of the Energy Transfer between Fluorescent Proteins Connected via Flexible Peptide Linkers", Biochemistry, vol. 45, pp. 13183-13192, 2006.
J. Christopher Anderson et al., "BglBricks: A flexible standard for biological part assembly", Anderson et al. Journal of Biological Engineering 2010, 4:1.
Charles Yanofsky et al., "Repression Is Relieved I3efore Attenuation in the trp Operon of *Escherichia coli* as Tryptophan Starvation Becomes Increasingly Severe", Journal of Bacteriology, Jun. 1984, p. 1018-1024.

(Continued)

*Primary Examiner* — Christian L Fronda
(74) *Attorney, Agent, or Firm* — PL Law Group, PLLC

(57) ABSTRACT

The present invention relates to an Fe—S fusion protein acting as an electron transport chain, a novel carbon monoxide:formate oxidoreductase (CFOR) including the Fe—S fusion protein, novel *Thermococcus* strain BCF12 transformed with CFOR, and the use thereof. According to the present invention, two different enzymes may be physically linked directly to each other through the Fe—S fusion protein of the present invention, and thus electrons generated from any one enzyme may be transported directly to another enzyme through the Fe—S cluster of the Fe—S fusion protein. Accordingly, a reaction that produces a target substance with high efficiency by directly supplying electrons necessary for the production of the target substance is possible without leakage of electrons generated in any one enzyme. In addition, the present invention has an advantage in that the overall enzyme reaction rate and yield can be dramatically improved using a new electron transport reaction. Furthermore, it is possible to ensure the stability of each enzyme by allowing the enzymes to exist in a physically fixed state in cells.

2 Claims, 12 Drawing Sheets

Specification includes a Sequence Listing.

(56) References Cited

OTHER PUBLICATIONS

Herskowitz, I. et al., "The Lysis-Lysogeny Decision of Phage X: Explicit Programming and Responsiveness", Ann. Rev. Genet., 14:399-445 (1980).

Chen, H. Y., et al., "Vectors, promoters, and expression of genes in chick embryos", Journal of Reproduction and fertility, vol. 41, 1990, (Abstract is submitted herewith).

Cohen, S.N. et al., "Nonchromosomal Antibiotic Resistance in Bacteria: Genetic Transformation of *Escherichia coli* by R-Factor DNA*", Proc. Natl. Acac. Sci. USA, vol. 69, pp. 2110-2114, 1972.

Donald B. Smith et al., "Signle-step purification of polypeptides expressed in *Escherichia coli* as fusions with glutathione S-transferse", Gene, vol. 67, 1988 (Abstract is submitted herewith.).

Dower, W. J et al., "High efficiency transformation of *E.coli* by high voltage electroporation", Nucleic. Acids Res., vol. 16, pp. 6127-6145, 1988.

Hanahan, D., "Studies on transformation of *Escherichia coli* with plasmids", Journal of Mol. Biol., vol. 166, 1983 (Abstract is submitted herewith.).

Tai-Kin, Wong et al,"Appearnace of beta-lactamase activity in animal cells upon liposome-mediated gene transfer", Gene, vol. 10, 1980 (Abstract is submitted herewith.).

Proudman J.A., "The Quest for Transgenic Poultry: Birds Are Not Mice With Feathers", R. Renaville and A. Burny (eds.), Biotechnology in Animal Husbandry, 283-299. (Abstract is submitted herewith.).

\* cited by examiner

Fe-S FUSION PROTEIN ACTING AS ELECTRON TRANSFER CHAIN, CARBON MONOXIDE FORMATE REDOX ENZYME MEDIATED THROUGH FES FUSION PROTEIN, STRAIN BCF12 DERIVED FROM *THERMOCOCCUS* WHEREIN ENZYME IS TRANSFORMED, AND USE THEREOF

GOVERNMENT LICENSE RIGHTS

This invention was made with Korean government support (i) under Project Grant No. PE99622 (Research Project Name: Institutional Purpose Project) (contribution rate: 80%) support awarded by Ministry of Oceans and Fisheries (Research management institution: Korea Institute of Ocean Science and Technology; and Supervision Institution: Korea Institute of Ocean Science and Technology) for the Research subject of "Elucidation and application of carbon metabolic process in non-photosynthetic marine and extreme microorganisms", (ii) under Project Grant No. 1711066286 (Research Project Name: Development (R&D) of technologies in response to climate change) (contribution rate: 10%) support awarded by Ministry of Science and ICT (Research management institution: National Research Foundation of Korea; and Supervision Institution: Korea Institute of Ocean Science and Technology) for the Research subject of "Development of acetogen strain for producing 2,3-BDO using CO", and (iii) under Project Grant No. 1525006521 (Research Project Name: Polar and ocean science research) (contribution rate: 10%) support awarded by Ministry of Oceans and Fisheries (Research management institution: National Research Foundation of Korea; and Supervision Institution: Korea Institute of Marine Science & Technology Promotion) for the Research subject of "Understanding for the deep-sea hydrothermal life system of the Indian Ocean Mid-Ocean Ridge". The Korean government has certain rights in the invention.

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2018/014807, filed Nov. 28, 2018, which claims priority to the benefit of Korean Patent Application Nos. 10-2018-0138475 filed on Nov. 12, 2018, 10-2018-0138467 filed on Nov. 12, 2018 and 10-2018-0138462 filed on Nov. 12, 2018 in the Korean Intellectual Property Office, the entire contents of which are incorporated herein by reference.

REFERENCE TO AN ELECTRONIC SEQUENCE LISTING

A sequence listing electronically submitted with the present application on Dec. 3, 2024 as an ASCII text file named 20241203_Q49021YG01_TU_SEQ.TXT, created on Dec. 3, 2024 and having a size of 45,902 bytes, is incorporated herein by reference in its entirety.

BACKGROUND

1. Technical Field

The present invention relates to an Fe—S fusion protein acting as an electron transport chain, a novel carbon monoxide:formate oxidoreductase (CFOR) including the Fe—S fusion protein, novel *Thermococcus* strain BCF12 transformed with CFOR, and the use thereof.

2. Background Art

With the breakthrough development of genetic engineering technology, the production of biomaterials by biological processes has gradually replaced petrochemical processes. The production of biomaterials by methods of applying bioconversion processes has advantages in that cheap renewable resources may be used as raw materials, and the generation of greenhouse gases such as carbon dioxide may be minimized, thus solving environmental problems. Accordingly, in recent years, there have been increasing studies on the development of related strains and improvement in processes for the production of biomaterials by bioprocesses.

Specifically, as methods of generating regulatory mutant strains, there have been used various techniques of increasing the production efficiency of target substances by creating new metabolic pathways or manipulating/changing pathways included in metabolic processes. These techniques are based on the premise that the expression or activity of one or more target proteins (or enzymes) related to the synthesis of a specific target product is promoted or inhibited. For example, for a recombinant microorganism having an increased ability to produce butanol, Korean Patent Application Publication No. 10-2014-0064469 discloses a microorganism in which the expression or activity of a protein (or enzyme) involved in a pathway that converts acetyl-CoA to acetate is inhibited and the expression or activity of a protein (or enzyme) involved in a pathway that converts acetyl-CoA to butyryl-CoA is promoted. In addition, Japanese Patent No. 4760951 attempted to improve the production efficiency of butanol by introducing, into a microorganism, enzymes such as 3-hydroxybutyryl-CoA dehydrogenase (HBD), 3-hydroxybutyryl-CoA dehydratase (CRT), trans-enoyl-CoA reductase (TER), and aldehyde/alcohol dehydrogenase (AdhE2), which are involved in butanol synthesis.

However, in the above-described conventional arts, intermediate products necessary for the production pathway of the substance to be synthesized by reactions may be accumulated in a microorganism, but there are disadvantages in that, since various converting enzymes in addition to the enzymes involved in the synthesis pathway of the substance to be synthesized exist in cells, the production efficiency of the substance is low, and above all, it is not possible to directly create a new synthetic pathway that can directly produce the target substance to be produced and does not exist in nature, or to create a reaction that directly synthesizes the target substance.

In order to solve these problems, Korean Patent Application Publication No. 10-2017-0024466 and the like discloses a system in which the physical gap existing between enzymes related to the biosynthesis of the target substance is narrowed in order to increase the synthesis efficiency of the target substance, so that intermediate products may immediately participate in reactions, thus solving the problem that accumulation of the intermediate products is interfered with by other enzymes. However, the method of increasing the activities of enzymes through an indirect method of simply narrowing the physical gap existing between biosynthesis-related enzymes has a fundamental problem in that it does not affect the electron transport or redox reactions of complex enzymes, and thus an increase in enzyme activity beyond a certain level cannot be expected.

Accordingly, the present inventors have conducted on a system to which immediate and direct electron transport between enzymes related to the biosynthesis of a target substance may be coupled so that it is possible to increase the synthesis efficiency of the target substance and to create a reaction that can directly produce the target substance to be produced and does not exist in nature. As a result, the present inventors have developed an Fe—S fusion protein formed by covalently linking two or more Fe—S proteins through a flexible linker so that Fe—S protein may act as an electron transport chain functioning as a channel through which electrons, and have synthesized a novel carbon monoxide: formate oxidoreductase (CFOR), which is not found in nature, using the Fe—S fusion protein, and have found that, when the synthesized CFOR is introduced into a *Thermococcus* BCF12 strain, the strain may produce the target substance formate with high yield and in high yield, thereby completing the present invention.

SUMMARY

Therefore, an object of the present invention is to provide an Fe—S fusion protein obtained by linking two or more Fe—S proteins and having an electron transport function, a novel carbon monoxide:formate oxidoreductase including the same, and a method of producing formate using the same.

Other objects and advantages of the present invention will be more apparent from the following detailed description, the appended claims and the accompanying drawings.

In accordance with one aspect of the present invention, the present invention provides an Fe—S fusion protein comprised of: a flexible linker having any one amino acid sequence selected from among SEQ ID NOs: 1 to 6; and two or more Fe—S proteins, each including any one amino acid sequence selected from among SEQ ID NOs: 7 to 11, the Fe—S fusion protein being formed by covalently linking the two or more Fe—S proteins through the flexible linker and acting as an electron transport chain functioning as a channel through which electrons move.

The Fe—S fusion protein may be variants or fragments of amino acids having different sequences by deletion, insertion, substitution or a combination thereof of amino acid residues within a range that does not affect the function of the Fe—S fusion protein. In addition, amino acid exchange at protein or peptide level that does not change the activity of the Fe—S fusion protein as a whole is known in the art. In some cases, the Fe—S fusion protein may be modified by phosphorylation, sulfation, acrylation, glycosylation, methylation, farnesylation, or the like.

The term "peptide" as used herein refers to a chain-type polymer formed by joining 4 to 1,000 amino acid residues together by peptide bonds, and may be used interchangeably with the term "polypeptide".

As used herein, the term "polynucleotide" refers to a polymer compound in which nucleotides, which are chemical monomers, each consisting of three parts (base, sugar, and phosphoric acid), are linked together in a chain form through a plurality of phosphate ester bonds.

In the present invention, the Fe—S fusion protein is one in which two different Fe—S proteins are linked together through the flexible linker.

As used herin, the term "Fe—S protein (iron-sulfur protein)" refers to a protein characterized by the presence of an "Fe—S cluster" containing sulfide-linked di-, tri-, or tetra-iron centers in variable oxidation states.

The "Fe—S cluster" appears in metalloproteins such as ferredoxins, and is found in various proteins such as NADH dehydrogenase, hydrogenases, coenzyme Q-cytochrome C reductase, succinate-coenzyme Q reductase, and nitrogenase. The "Fe—S protein (iron-sulfur protein)" comprised of the "Fe—S cluster" is best known for its role in the redox reaction of electron transport in mitochondria.

As used herein, the term "electron transport chain" refers to an electron transport channel in which two or more "Fe—S proteins" are covalently linked in tandem in a chain form through a flexible linker. As used herein, the term "Fe—S fusion protein" serving as an electron transport chain refers to a new fusion protein synthesized by the present inventors, which is comprised of two or more "Fe—S proteins" covalently linked through a flexible linker and serves as a unit element to form the electron transport chain.

In the Fe—S fusion protein of the present invention, the Fe—S fusion protein is one in which two or more Fe—S proteins are covalently linked together through a flexible linker having any one amino acid sequence selected from among SEQ ID NOs: 1 to 6 shown in Table 1 below. Examples of flexible linkers having a function similar to that of the above-described flexible linker are described in Chen X, et al. 2013. Adv Drug Deliv Rev 65:1357-69.

TABLE 1

| SEQ ID NO | Flexible linker sequence |
|---|---|
| 1 | $(GGGSG)_1$: GGGGS |
| 2 | $(GGGSG)_2$: GGGSGGGGSG |
| 3 | $(GGGSG)_3$: GGGSGGGSGGGGGS |
| 4 | $(GGGSG)_4$: GGGSGGGSGGGGSGGGGS |
| 5 | $(G)_5$: GGGGG |
| 6 | $(G)_6$: GGGGGG |

In addition, contents related to peptide linkers including the flexible linkers are disclosed in detail in "Toon H. Evers et al., 2006, J. Christopher Anderson et al., 2010", the disclosure of which is incorporated herein by reference.

Meanwhile, when Fe—S proteins enter a reduced state by accepting electrons, a hyperfine magnetic field of about 180 kG is formed. Fe—S proteins, which are linked together by the flexible linker and located within a short distance from each other, are tightly bound to the electron-accepted Fe—S proteins due to the effect of the formed hyperfine magnetic field. For this reason, the physical distance between the electron transport chains of the Fe—S proteins disappears, and as a result, the "Fe—S fusion protein" may be used as a single electron transport channel.

As used herein, the term "operatively linked" refers to a functional linkage between a nucleic acid expression control sequence (such as a promoter sequence, a signal sequence, or array of transcription factor binding sites) and another nucleic acid sequence, wherein the expression control sequence controls transcription and/or translation of the other nucleic acid sequence.

In addition, in the Fe—S fusion protein of the present invention, each of the Fe—S proteins may include any one selected from among the amino acid sequences of SEQ ID NOs: 7 to 11 or a combination of the amino acid sequences. The Fe—S proteins include the cysteine motifs of SEQ ID NOs: 7 to 11 shown in Table 2 below in order to form an Fe—S cluster. The present inventors compared 190 known Fe—S proteins and selected cysteine motifs having the amino acid sequences of SEQ ID NOs: 7 to 11. In addition, the present inventors confirmed through the Examples that an Fe—S fusion protein produced by covalently linking Fe—S proteins containing these motifs through a flexible linker acts as an electron transport chain.

TABLE 2

| SEQ ID NO | Fe-S protein |
|---|---|
| 7 | CXXCXXXXCXXXC |
| 8 | CXXCXXCXXXC |
| 9 | CXXCXXCXXXXC |
| 10 | CXXC |
| 11 | CXXXC |

In addition, in the Fe—S fusion protein of the present invention, the Fe—S fusion protein may be formed by covalently linking 2 to 5 Fe—S proteins together through a flexible linker.

Since the Fe—S fusion protein of the present invention acts as an electron transport chain functioning as a channel through which electrons move, two different enzymes may be linked to each other by the Fe—S fusion protein of the present invention. In this case, since electrons generated in any one enzyme may be transported to another enzyme to directly mediate a redox reaction, it is possible to activate the enzyme reaction in a manner not found in nature and to produce a target substance with high efficiency and in high yield.

In this case, the enzyme that generates the electrons to be transported may be operatively linked to the C-terminus of the Fe—S fusion protein, and the enzyme that accepts the electrons may be operatively linked to the N-terminus of the Fe—S fusion protein, so that the electrons may be transported through the Fe—S fusion protein.

For example, as shown in FIG. 1, when the enzyme that generates electrons to be transported is CO dehydrogenase (CODH) and the enzymes that accepts the electrons is formate dehydrogenase (Fdh), the electrons generated in the CO dehydrogenase may be transported to the formate dehydrogenase, thus producing formate with high efficiency and in high yield.

In addition, even when the enzyme that accepts electrons is replaced with succinate dehydrogenase, dimethyl sulfoxide (DMSO) reductase, hydrogenase or the like, the electron transport function may be maintained. In this case, depending on the types of enzymes (succinate dehydrogenase, dimethyl sulfoxide (DMSO) reductase, and hydrogenase), succinic acid production, DMSO reduction and hydrogen production may be performed with high efficiency and in high yield.

In addition, the Fe—S fusion protein of the present invention may further include a tag in order to facilitate isolation and purification. The fusion protein of the present invention may be tagged with various detectable tags. The tags include, but are not limited to, His(n), flag, c-Myc, HA, V5, VSV-G and HSV. The tag refers to a polypeptide sequence consisting of 3 to 40 amino acids, and imparts specific affinity to the fusion protein of the present invention, a peptide, a protein ligand (e.g., the fusion protein of the present invention), or a non-peptide ligand. In addition, tags that may be used in the present invention may include fluorescent tags, luminescent tags and chromogenic tags.

In the Fe—S fusion protein of the present invention, the Fe—S fusion protein may have the amino acid sequence of SEQ ID NO: 13.

The present invention also includes proteins and variants thereof or active fragments thereof, which have substantially the same amino acid sequence as the protein including the amino acid sequence of SEQ ID NO: 13. The term "substantially the same amino acid sequence refers to those having an amino acid sequence homology of at least 80%, preferably at least 90%, most preferably at least 95%, but is not limited thereto, and those having the same enzymatic activity while having an amino acid sequence homology of at least 80% are included within the scope of the present invention.

According to another aspect of the present invention, the present invention provides a nucleotide sequence encoding the Fe—S fusion protein of the present invention. Specifically, the nucleotide sequence may be the nucleotide sequence of SEQ ID NO: 17 encoding the amino acid sequence of SEQ ID NO: 13, but is not limited thereto, and it will be obvious to those skilled in the art that any nucleotide sequence encoding the Fe—S fusion protein may be used.

A gene encoding the Fe—S fusion protein of the present invention, a variant thereof, or an active fragment thereof may be variously modified in its coding region within a range that does not change the amino acid sequence of a protein expressed from the coding region, and may also be variously mutated by substitution, deletion, insertion or a combination thereof in regions other than the coding region within a range that does not affect the expression of the gene, and these mutated genes are also included within the scope of the present invention. Thus, the present invention includes nucleotide sequences and fragments thereof, which are substantially the same as the nucleotide sequence encoding the Fe—S fusion protein. The term "substantially the same nucleotide sequences" refers to those having a sequence homology of at least 80%, preferably at least 90%, most preferably at least 95%, but is not limited thereto, and those having a sequence homology of at least 85% are included within the scope of the present invention, as long as proteins encoded thereby have the same enzymatic activity.

According to still another aspect of the present invention, the present invention provides a recombinant vector including: (a) the nucleotide sequence encoding the Fe—S fusion protein; and (b) a promoter operatively linked to the nucleotide sequence. As used herein, the term "promoter" refers to a DNA sequence that controls the expression of a coding sequence or functional RNA. In the recombinant expression vector of the present invention, the nucleotide sequence encoding a substance to be expressed (i.e., Fe—S fusion protein) is operatively linked to the promoter.

The vector system of the present invention may be constructed by various methods known in the art, and a specific method therefor is disclosed in Sambrook et al., Molecular Cloning, A Laboratory Manual, Cold Spring Harbor Laboratory Press (2001), which is incorporated herein by reference.

When the expression vector of the present invention uses a prokaryotic cell as a host, it generally includes a strong promoter (e.g., tac promoter, lac promoter, lacUV5 promoter, lpp promoter, pL promoter, pR promoter, rac5 promoter, amp promoter, recA promoter, SP6 promoter, trp promoter, T7 promoter, etc.) capable of directing transcription, a ribosome binding site for initiation of translation, and a transcription/translation termination sequence. At this time, the bacterial replication origin may be selected from replication origins that are well known in the art to be useful in the stable bacterial replication of long DNA inserts, and examples thereof include, but are not limited to, ColE1, F-factor, and P1 replicon. As the bacterial selection marker of the present invention, a bacterial selection marker gene known in the art may be used. Examples of the bacterial selection marker gene include, but are not limited to, genes that confer resistance to antibiotics, such as ampicillin, kanamycin, tetracycline, Zeocin, neomycin, hygromycin, and chloramphenicol. Where *E. coli* is used as a host cell, the promoter and operator region for the tryptophan biosynthesis pathway (Yanofsky, C., J. Bacteriol., 158:1018-1024 (1984)) and the leftward promoter from phage λ (pLλ promoter, Herskowitz, I. and Hagen, D., Ann. Rev. Genet., 14:399-445 (1980)) may be used as regulating sequences.

In addition, where the recombinant vector of the present invention is applied to eukaryotic cells, promoters that may be used can control transcription of the substance to be expressed in the present invention, and include promoters derived from mammalian viruses and promoters derived from mammalian cell genomes. Examples of the promoter include, but are not limited to, cytomegalovirus (CMV) promoter, adenovirus late promoter, vaccinia virus 7.5K promoter, SV40 promoter, tk promoter of HSV, RSV promoter, EF1 alpha promoter, metallothionein promoter, beta-actin promoter, human IL-2 gene promoter, human IFN gene promoter, human IL-4 gene promoter, human lymphotoxin gene promoter, and human GM-CSF gene promoter.

Preferably, the recombinant vector that is used in the present invention includes a polyadenylation sequence (e.g., bovine growth hormone terminator or SV40-derived polyadenylation sequence).

The vector may include a selectable marker for selecting a host cell containing the vector. The selectable marker is used to select a cell transformed with the vector, and examples thereof include markers providing a selectable phenotype such as drug resistance, auxotrophy, resistance to a cytotoxic agent, or expression of a surface protein. Since only cells expressing the selectable marker survive in an environment treated with the selective agent, the transformed cell may be selected. In addition, where the vector is a replicable expression vector, the vector may include a replication origin which is a specific nucleic acid sequence initiating replication.

Expression vectors that may be used in bacterial hosts include bacterial plasmids obtained from *Escherichia coli*, such as pET, pRSET, pBluescript, pGEX2T, pUC vector, col E1, pCR1, pBR322, pMB9, and derivatives thereof, plasmids having a larger range of host, such as RP4, phage DNA exemplified by significantly various phage lambda derivatives, such as λgt10 and λgt11, NM989, and other DNA phages such as M13 and filamentous single stranded DNA phage. In particular, for expression in *E. coli*, a DNA sequence encoding an anthranilate synthase (TrpE) and a C-terminal polylinker may be included, and other expression vector systems are based on beta-galactosidase (pEX); lambda PL maltose binding protein (pMAL); and glutathione S-transferase (pGST) (Gene 67:31, 1988; Peptide Research 3:167, 1990).

According to yet another aspect of the present invention, the present invention provides a cell transformed with the recombinant vector of the present invention. The recombinant vector is inserted into a host cell to form a transformant or a recombinant microorganism. Suitable host cells for the vector may be prokaryotic cells such as *E. coli, Bacillus subtilis, Streptomyces* sp., *Pseudomonas* sp., *Proteus mirabilis* or *Staphylococcus* sp., and may also be Archaea such as *Thermococcus onnurineus*. In addition, the host cells may be fungi such as *Aspergillus* sp., yeasts such as *Pichia pastoris, Saccharomyces cerevisiae, Schizosaccharomyces* sp. and *Neurospora crassa*, and eukaryotic cells such as other lower eukaryotic cells, and cells of higher eukaryotes such as cells from insects.

Delivery of the vector of the present invention into the host cell may be performed using various methods known in the art. For example, where the host cells are eukaryotic cells, the delivery may be performed by a $CaCl_2$ method (Cohen, S. N. et al., Proc. Natl. Acac. Sci. USA, 69:2110-2114(1972)), a Hanahan's method (Cohen, S. N. et al., Proc. Natl. Acac. Sci. USA, 69:2110-2114(1972); and Hanahan, D., J. Mol. Biol., 166:557-580(1983)), and an electroporation method (Dower, W. J. et al., Nucleic. Acids Res., 16:6127-6145(1988)). Where the host cells are prokaryotic cells, the delivery may be performed using transduction, electroporation, lipofection, microinjection, particle bombardment, yeast spheroplast/cell fusion used in YAC, *Agrobacterium*-mediated transformation used in plant cells, or the like.

In addition, the production of animal cells using the recombinant expression vector of the present invention may be performed by a gene transfer method that is commonly known in the art. Examples of the method include, but are not limited to, electroporation, liposome-mediated transfer (Wong, et al., 1980), and retrovirus-mediated transfer (Chen, H. Y., et al., (1990), J. Reprod. Fert. 41:173-182; Kopchick, J. J. et al., (1991) Methods for the introduction of recombinant DNA into chicken embryos. In Transgenic Animals, ed. N. L. First & F. P. Haseltine, pp. 275-293, Boston; Butterworth-Heinemann; Lee, M.-R. and Shuman, R. (1990) Proc. 4th World Congr. Genet. Appl. Livestock Prod. 16, 107-110).

According to another aspect of the present invention, the present invention provides a method for producing an Fe—S fusion protein, the method including a step of expressing the Fe—S fusion protein by culturing the recombinant microorganism of the present invention.

According to another aspect of the present invention, the present invention provides a carbon monoxide:formate oxidoreductase (CFOR) wherein CO dehydrogenase (CODH) and formate dehydrogenase (Fdh) are linked together through an Fe—S fusion protein, the carbon monoxide: formate oxidoreductase (CFOR) including: an Fe—S fusion protein acting as an electron transport chain functioning as a channel through which electrons move, and formed by covalently linking two or more Fe—S proteins through a flexible linker having any one amino acid sequence selected from among SEQ ID NOs: 1 to 6; a CO dehydrogenase (CODH) operatively linked to the C-terminus of the Fe—S fusion protein; and a formate dehydrogenase (Fdh) operatively linked to the N-terminus of the Fe—S fusion protein, wherein electrons generated in the CO dehydrogenase are transported to the formate dehydrogenase (Fdh) through the Fe—S fusion protein.

In the carbon monoxide:formate oxidoreductase (CFOR), the CO dehydrogenase (CODH) and the formate dehydrogenase (Fdh) may be variants or fragments of amino acids having different sequences by deletion, insertion, substitution or a combination thereof of amino acid residues within a range that does not affect the protein functions of the CO dehydrogenase (CODH) and the formate dehydrogenase (Fdh). In addition, amino acid exchange at protein or peptide level that does not change the activities of the CO dehydrogenase (CODH) and the formate dehydrogenase (Fdh) as a whole is known in the art. In some cases, the CO dehydrogenase (CODH) and the formate dehydrogenase (Fdh) may be modified by phosphorylation, sulfation, acrylation, glycosylation, methylation, farnesylation, or the like.

In the present invention, the CO dehydrogenase (CODH) and the formate dehydrogenase (Fdh) are linked together through the Fe—S fusion protein, wherein the Fe—S fusion protein is one in which two different Fe—S proteins are linked together by the flexible linker.

In the carbon monoxide:formate oxidoreductase (CFOR) of the present invention, the Fe—S fusion protein is one in which two or more Fe—S proteins are covalently linked through a flexible linker having any one amino acid sequence selected from among SEQ ID NOs: 1 to 6.

In addition, in the carbon monoxide:formate oxidoreductase (CFOR) of the present invention, each of the Fe—S proteins may include any one selected from among the amino acid sequences of SEQ ID NOs: 7 to 11 or a combination of the amino acid sequences.

In addition, in the carbon monoxide:formate oxidoreductase (CFOR) of the present invention, the Fe—S fusion protein may be formed by covalently linking 2 to 5 Fe—S proteins together through the flexible linker.

In the carbon monoxide:formate oxidoreductase (CFOR) of the present invention, the CO dehydrogenase (CODH) may be a gene derived from any one strain selected from the group consisting of *Thermococcus onnurineus* NA1, *Thermococcus* sp. CH5, *Thermococcus guaymasensis*, *Thermococcus profundus*, *T. hermococcus radiotolerans*, *Thermococcus gammatolerans*, *Thermococcus barophilus*, *Thermococcus* AM4, *Methanothermobacter thermoautotrophicus*, *Archaeoglobus fulgidus*, *Clostridium autoethanogenum*, *Clostridium ljungdahlii*, *Clostridium carboxidivorans*, *Oxobacter pfennigii*, *Peptostrep tococcus productus*, *Acetobacterium woodii*, *Eubacterium limosum*, *Butyribacterium methylotrophicum*, *Rubrivivax gelatinosus*, *Rhodopseudomonas palustris*, *Rhodospirillum rubrum*, *Citrobacter* sp Y19, *Methanosarcina barkeri*, *Methanosarcina acetivorans*, *Moorella thermoacetica*, *Moorella thermoautotrophica*, *Moorella* strain AMP, *Carboxydothermus hydrogenoformans*, *Carboxydibrachium pacificus*, *Carboxydocella sporoproducens*, *Carboxydocella thermoautotrophica*, *Thermincola carboxydiphila*, *Therinincola ferriacetica*, *Thermolithobacter carboxydivorans*, *Thermosinus carboxydivorans*, *Desulfotomaculum kuznetsovii*, *Desulfotomaculum thermobenzoicum* sub sp. *thermosyntrophicum*, and *Desulfotomaculum carboxydivorans*, and the formate dehydrogenase (Fdh) may be a gene derived from any one strain selected from the group consisting of *Thermococcus onnurineus* NA1, *Thermococcus fumicolans*, *Thermococcus* sp. CH5, *Thermococcus celericrescens*, *Thermococcus litoralis*, *Thermococcus pacificus*, *Thermococcus profundus*, *Thermococcus radiotolerans*, *Thermococcus stetteri*, *Thermococcus waiotapuensis*, *Thermococcus* sp AM4, *Thermococcus sibiricus*, *Thermococcus kodakarensis*, *Thermococcus gammatolerans*, *Thermococcus barophilus*, *Thermococcus* sp. 4557, *Pyrococcus furiosus*, *Pyrococcus abyssi*, *Pyrococcus yayanosii*, *Pyrococcus* sp. NA2, *Carboxydothermus hydrogenofomans*, *Rubrivivax gelatinosus*, *Escherichia coli*, *Rhodospirillum rubrum*, *Moorella thermoacetica*, *Clostridium autoethanogenum*, *Clostridium ljungdahlii*, *Acetobacterium woodii*, *Eubacterium limosum*, *Clostridium carboxidivorans*, and *Rhodpseudomonas palustris*.

In addition, in the carbon monoxide:formate oxidoreductase (CFOR) of the present invention, the Fe—S fusion protein acts as an electron transport chain functioning as an electron transport channel, and thus directly mediate a redox reaction. Thus, electrons generated in the CO dehydrogenase are transported directly to the formate dehydrogenase (Fdh). Even when the formate dehydrogenase (Fdh) is replaced with succinate dehydrogenase, dimethyl sulfoxide (DMSO) reductase, hydrogenase or the like, the electron transport function may be maintained. In this case, the functions of succinic acid production, DMSO reduction and hydrogen production are newly provided by succinate dehydrogenase, dimethyl sulfoxide (DMSO) reductase, and hydrogenase, which are used for replacement.

In addition the carbon monoxide:formate oxidoreductase (CFOR) of the present invention may further include a tag. A tag that may be included in the carbon monoxide:formate oxidoreductase (CFOR) is as described above with respect to a tag that may be included in the Fe—S fusion protein, description thereof will be omitted herein.

In the carbon monoxide:formate oxidoreductase (CFOR) of the present invention, the carbon monoxide:formate oxidoreductase (CFOR) may have the amino acid sequence of SEQ ID NO: 15 in which the CO dehydrogenase (CODH) of SEQ ID NO: 12, the Fe—S fusion protein of SEQ ID NO: 13 and the formate dehydrogenase (Fdh) of SEQ ID NO: 14 are operatively linked to one another.

The present invention includes proteins, variants thereof, or active fragments thereof, which have substantially the same amino acid sequences as the protein including the amino acid sequence of SEQ ID NO: 15. The term "substantially the same amino acid sequences" refers to those having an amino acid sequence homology of at least 80%, preferably at least 90%, most preferably at least 95%, but is not limited thereto, and those having the same enzymatic activity while having an amino acid sequence homology of at least 80% are included within the scope of the present invention.

According to another aspect of the present invention, the present invention provides a nucleotide sequence encoding the carbon monoxide:formate oxidoreductase (CFOR) of the present invention. Specifically, the nucleotide sequence may be, for example, the nucleotide sequence of SEQ ID NO: 16 encoding the amino acid sequence of SEQ ID NO: 15, but is not limited thereto, and it will be obvious to those skilled in the art that any nucleotide sequence encoding the carbon monoxide:formate oxidoreductase may be used.

A gene encoding the carbon monoxide:formate oxidoreductase (CFOR) of the present invention, a variant thereof, or an active fragment thereof may be variously modified in its coding region within a range that does not change the amino acid sequence of a protein expressed from the coding region, and may also be variously mutated by substitution, deletion, insertion or a combination thereof in regions other than the coding region within a range that does not affect the expression of the gene, and these mutated genes are also included within the scope of the present invention. Thus, the present invention includes nucleotide sequences and fragments thereof, which are substantially the same as the nucleotide sequence encoding the carbon monoxide:formate oxidoreductase (CFOR). The term "substantially the same nucleotide sequences" refers to those having a sequence homology of at least 80%, preferably at least 90%, most preferably at least 95%, but is not limited thereto, and those having a sequence homology of at least 85% are included within the scope of the present invention, as long as proteins encoded thereby have the same enzymatic activity.

According to another aspect of the present invention, the present invention provides a recombinant vector including: (a) a nucleotide sequence encoding the carbon monoxide: formate oxidoreductase (CFOR); and (b) a promoter operatively linked to the nucleotide sequence. As used herein, the term "promoter" refers to a DNA sequence that controls the expression of a coding sequence or functional RNA. In the recombinant expression vector of the present invention, the nucleotide sequence encoding a substance to be expressed (i.e., carbon monoxide:formate oxidoreductase is operatively linked to the promoter.

The vector system of the present invention may be constructed by various methods known in the art, and a specific method therefor is as described above with respect to the vector system into which the Fe—S fusion protein may be introduced, and thus description thereof will be omitted herein.

Another aspect of the present invention, the present invention provides a cell transformed with the recombinant vector of the present invention. The recombinant vector is inserted into a host cell to form a transformant or a recombinant microorganism. Suitable host cells for the vector and a method of delivering the vector of the present invention into the host cell are as described above with respect to the transformed cell into which the Fe—S fusion protein may be introduced, and thus description thereof will be omitted herein.

According to another aspect of the present invention, the present invention provides a method for producing a carbon monoxide:formate oxidoreductase (CFOR), the method including a step of expressing the carbon monoxide:formate oxidoreductase (CFOR) by culturing the recombinant microorganism of the present invention.

According to another aspect of the present invention, the present invention provides a method for producing formate, the method including steps of: (a) synthesizing formate from CO gas by supplying the CO gas in the presence of the carbon monoxide:formate oxidoreductase (CFOR) or the transformed cell; and (b) recovering the synthesized formate.

According to another aspect of the present invention, the present invention provides novel *Thermococcus* strain BCF12 (accession number: KCTC 13649BP). As demonstrated in an example of the present invention, novel *Thermococcus* strain BCF12 (accession number: KCTC 13649BP) is one transformed with the carbon monoxide: formate oxidoreductase (CFOR), and thus has an improved ability to produce formate.

The strain was deposited with the Korea Research Institute of Bioscience and Biotechnology on Sep. 21, 2018 under accession number KCTC 13649BP.

According to another aspect of the present invention, the present invention provides a method for producing a carbon monoxide:formate oxidoreductase (CFOR), the method including a step of expressing the carbon monoxide:formate oxidoreductase (CFOR) by culturing novel *Thermococcus* strain BCF12 (accession number: KCTC 13649BP) of the present invention.

According to another aspect of the present invention, the present invention provides a method for producing formate, the method including steps of: (a) synthesizing formate from CO gas by supplying the CO gas in the presence of the novel strain BCF12 (accession number: KCTC 13649BP) or the carbon monoxide:formate oxidoreductase (CFOR); and (b) recovering the synthesized formate.

As described above, two different enzymes may be physically linked directly to each other through the Fe—S fusion protein of the present invention, and thus electrons generated in any one enzyme may be transported directly to another enzyme through the Fe—S cluster of the Fe—S fusion protein.

In addition, the carbon monoxide:formate oxidoreductase (CFOR) of the present invention is produced by directly linking CO dehydrogenase (CODH) and formate dehydrogenase directly to each other through the Fe—S fusion protein consisting of Fe—S proteins, and thus electrons generated in the CO dehydrogenase may be transported directly to the formate dehydrogenase through the Fe—S cluster of the Fe—S fusion protein.

Accordingly, a reaction that produces formate with high efficiency through oxidation reaction of carbon monoxide by directly supplying electrons necessary for the formate dehydrogenase reaction in the conversion of carbon dioxide into formate is possible without leakage of generated electrons.

In addition, the present invention has an advantage in that the overall enzyme reaction rate and yield can be dramatically improved using a new carbon monoxide:formate oxidoreductase (CFOR) reaction. Furthermore, it is possible to ensure the stability of each enzyme by allowing the enzymes to exist in a physically fixed state in cells.

BRIEF DESCRIPTION OF THE DRAWINGS

[FIG. 5A: a schematic view of fdh3 and codh gene clusters present in the *T. onnurineus* NA1 genome and target genes used for cloning; FIG. 5B: construction of a fusion protein between TON_0541 and TON_1017. A schematic view showing cloning of strains to which a flexible linker consisting of one 'GGGGS (SEQ ID NO: 1)' amino acid moiety (*T. onnurineus* BCF01), a flexible linker consisting of two 'GGGGS (SEQ ID NO: 1)' amino acid moieties (*T. onnurineus* BCFO2), and a flexible linker consisting of three 'GGGGS (SEQ ID NO: 1)' amino acid moieties (*T. onnurineus* BCF03) were applied; FIG. 5C: construction of a fusion protein between TON_0540 and TON_1017. A schematic view showing cloning of a strain to which a flexible linker consisting of one 'GGGGS (SEQ ID NO: 1)' amino acid moiety (*T. onnurineus* BCF12) was applied].

DETAILED DESCRIPTION

Figure 1:
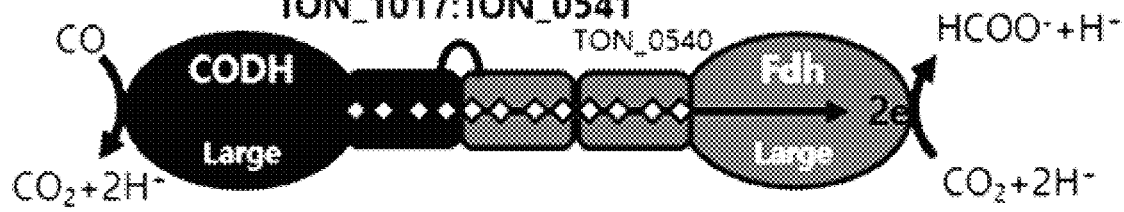
FIG. 1 illustrates the structure of a carbon monoxide: formate oxidoreductase (CFOR) of the present invention, and shows a series of processes in which electrons generated from the oxidation of CO gas by CO dehydrogenase (CODH) move through an Fe—S cluster (◇) present in the electron transport chain Fe—S fusion protein and is transported to the $CO_2$ reductase formate dehydrogenase (FDH), and $CO_2$ is converted into formate by an enzymatic reaction.
Figure 1:
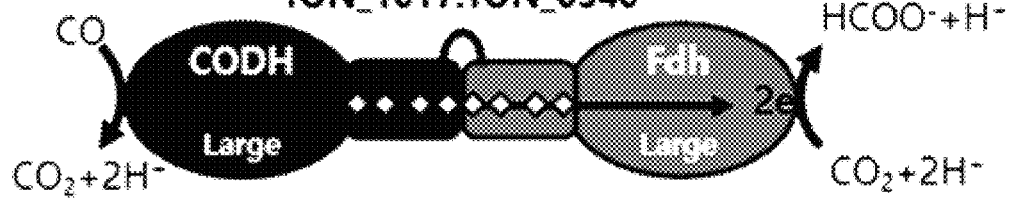
Figure 2:
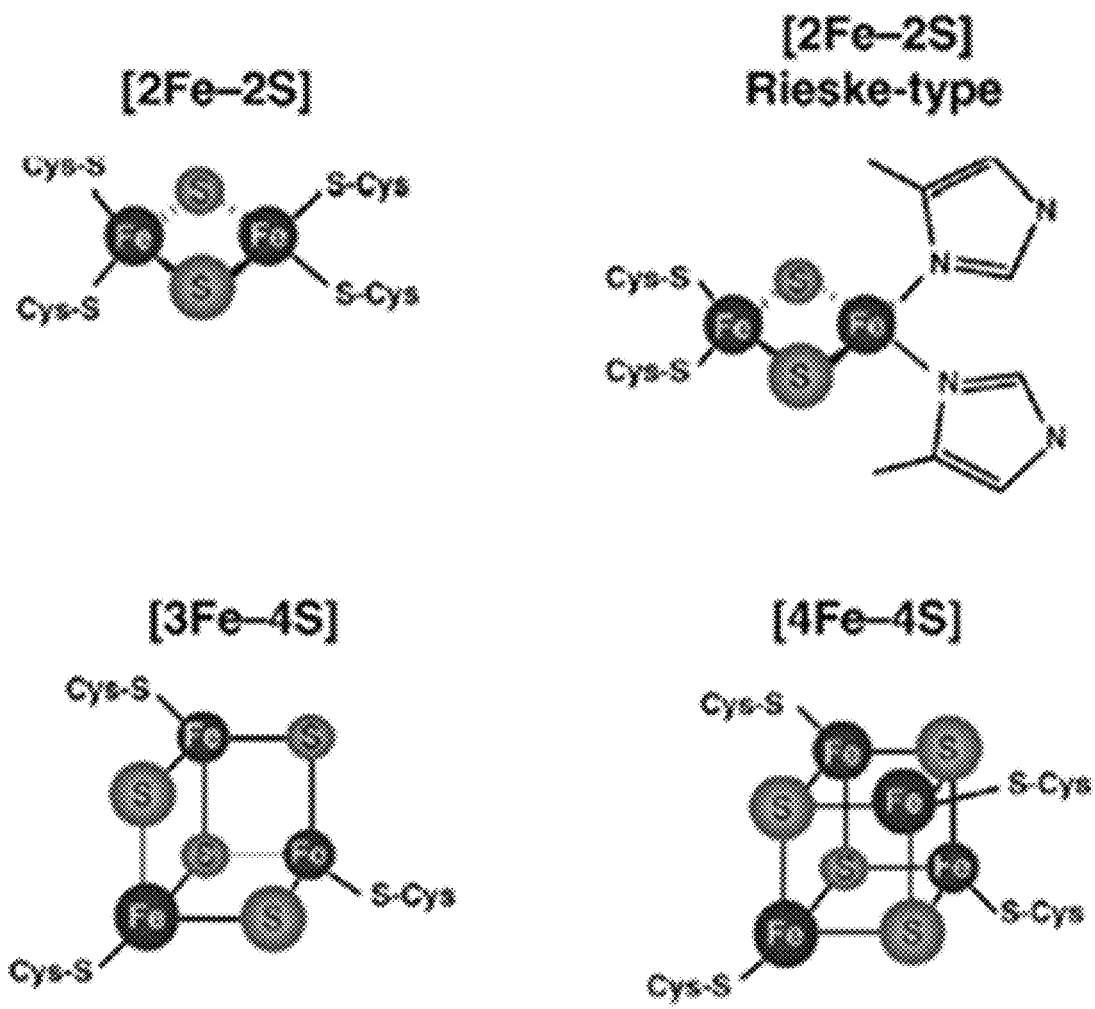
FIG. 2 is a schematic view illustrating the types of Fe—S clusters that are generally present in Fe—S protein (iron-sulfur protein).
Figure 3:
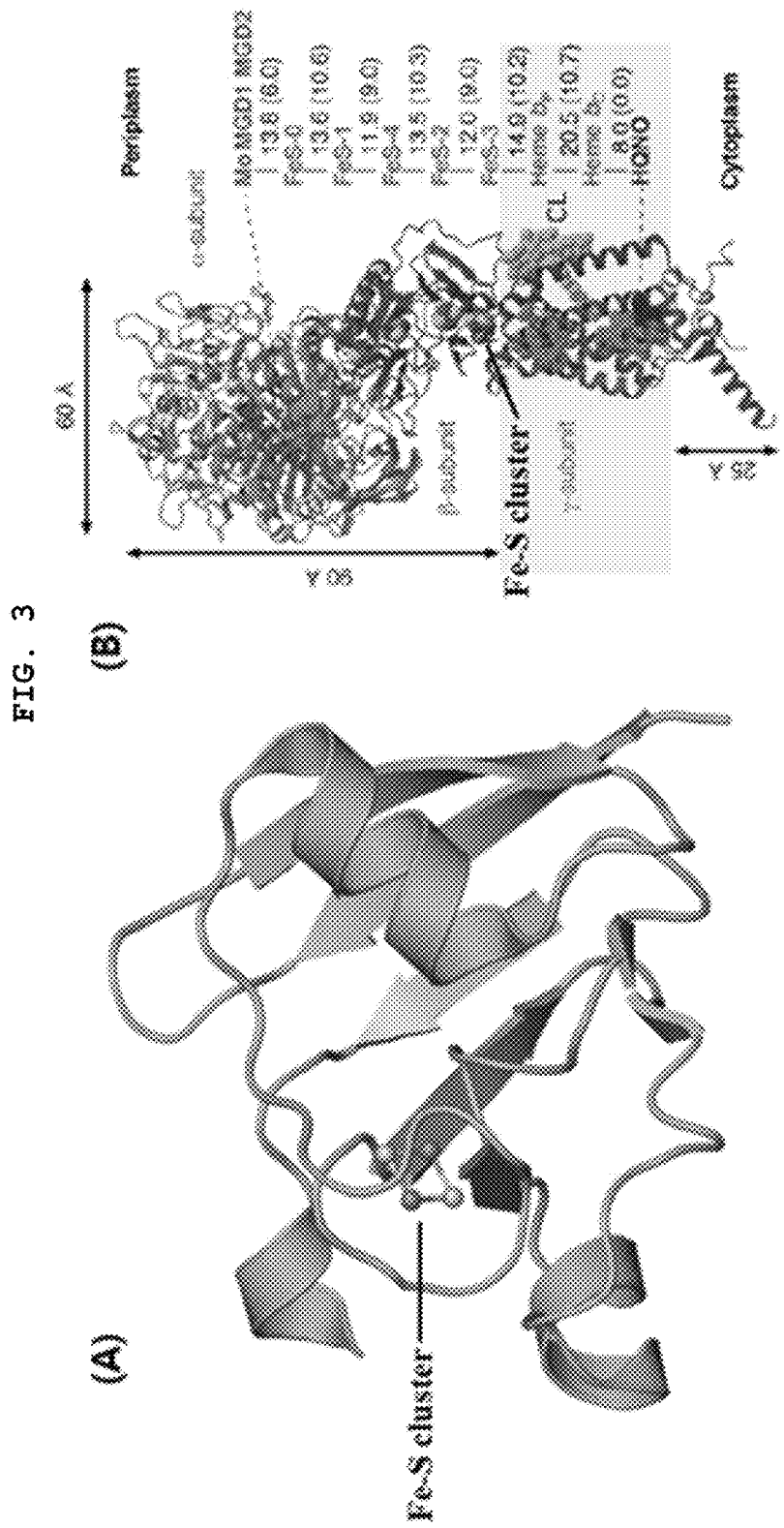
FIG. 3 shows ferredoxin ((A) of FIG. 3) containing an Fe—S cluster and the protein structure of formate dehydrogenase (FDH).
Figure 4:
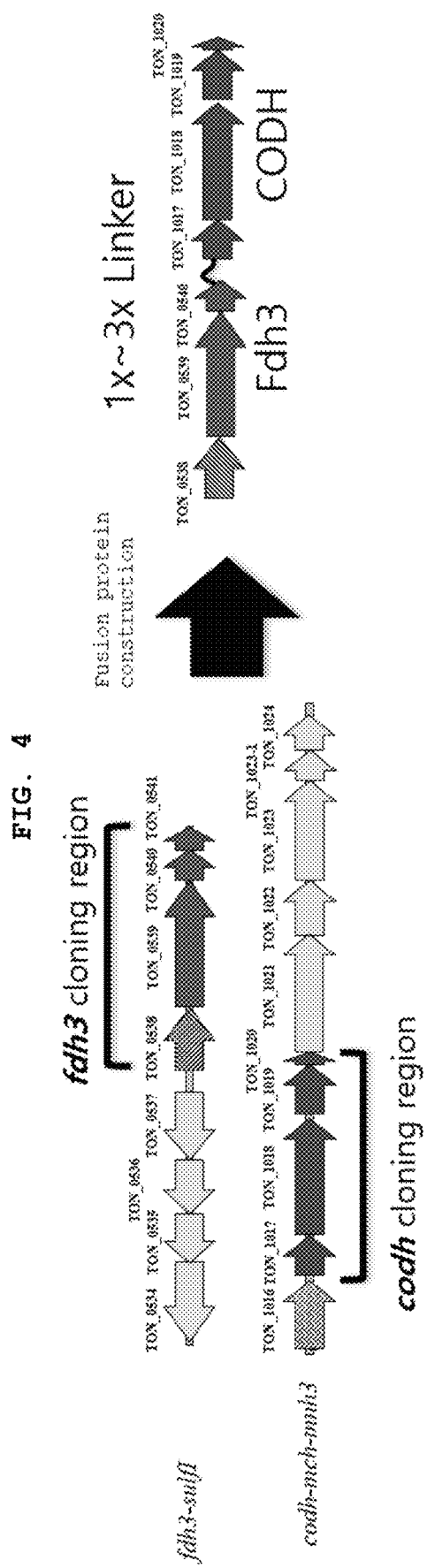
FIG. 4 shows a process of producing a carbon monoxide: formate oxidoreductase (CFOR) gene by recombination of CO dehydrogenase (CODH) and formate dehydrogenase.
Figure 5A:
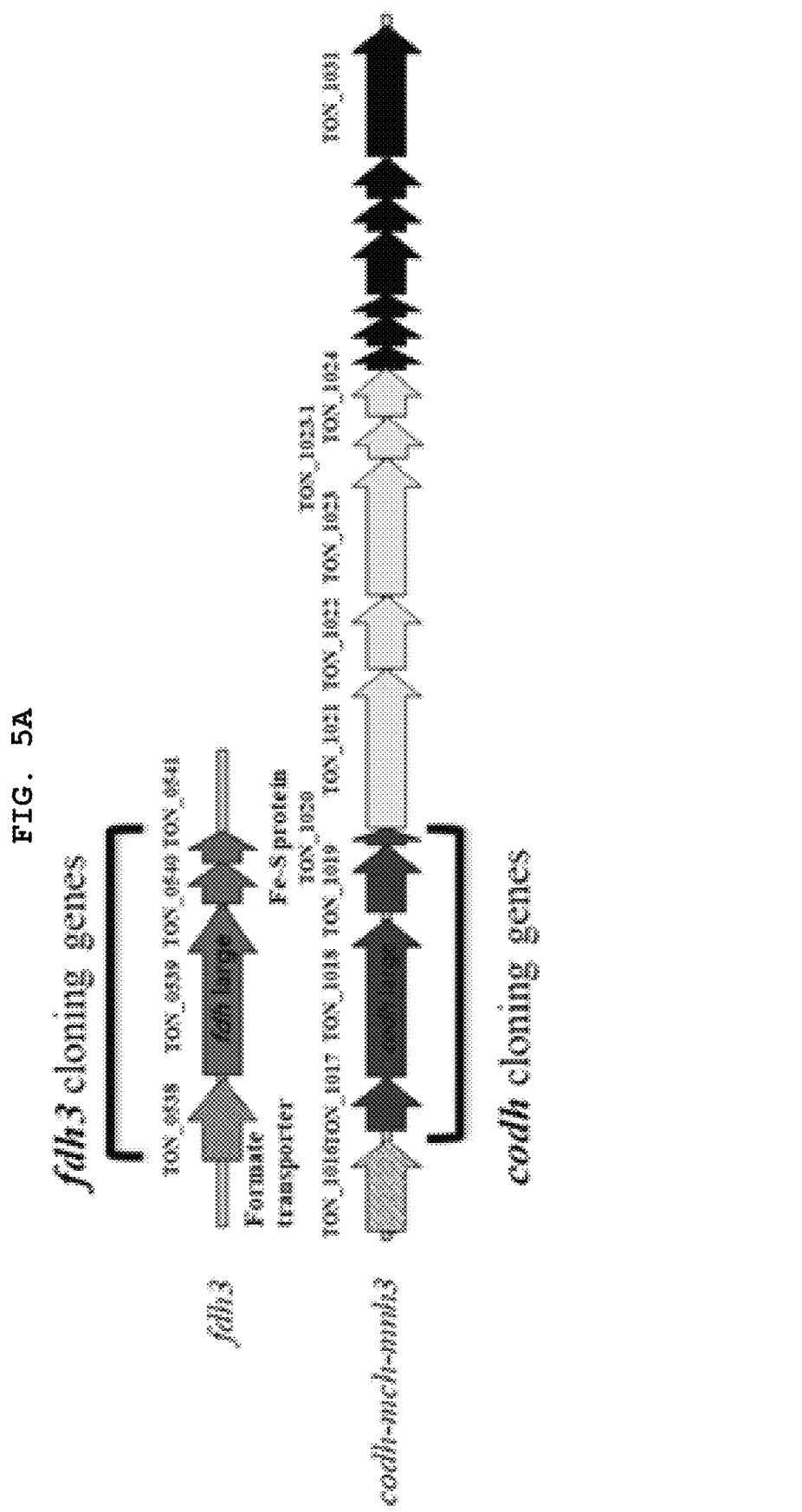
FIGS. 5A to 5C show the genetic structure of each transformant produced by inserting the carbon monoxide: formate oxidoreductase (CFOR) into the genome of a host cell
Figure 5B:
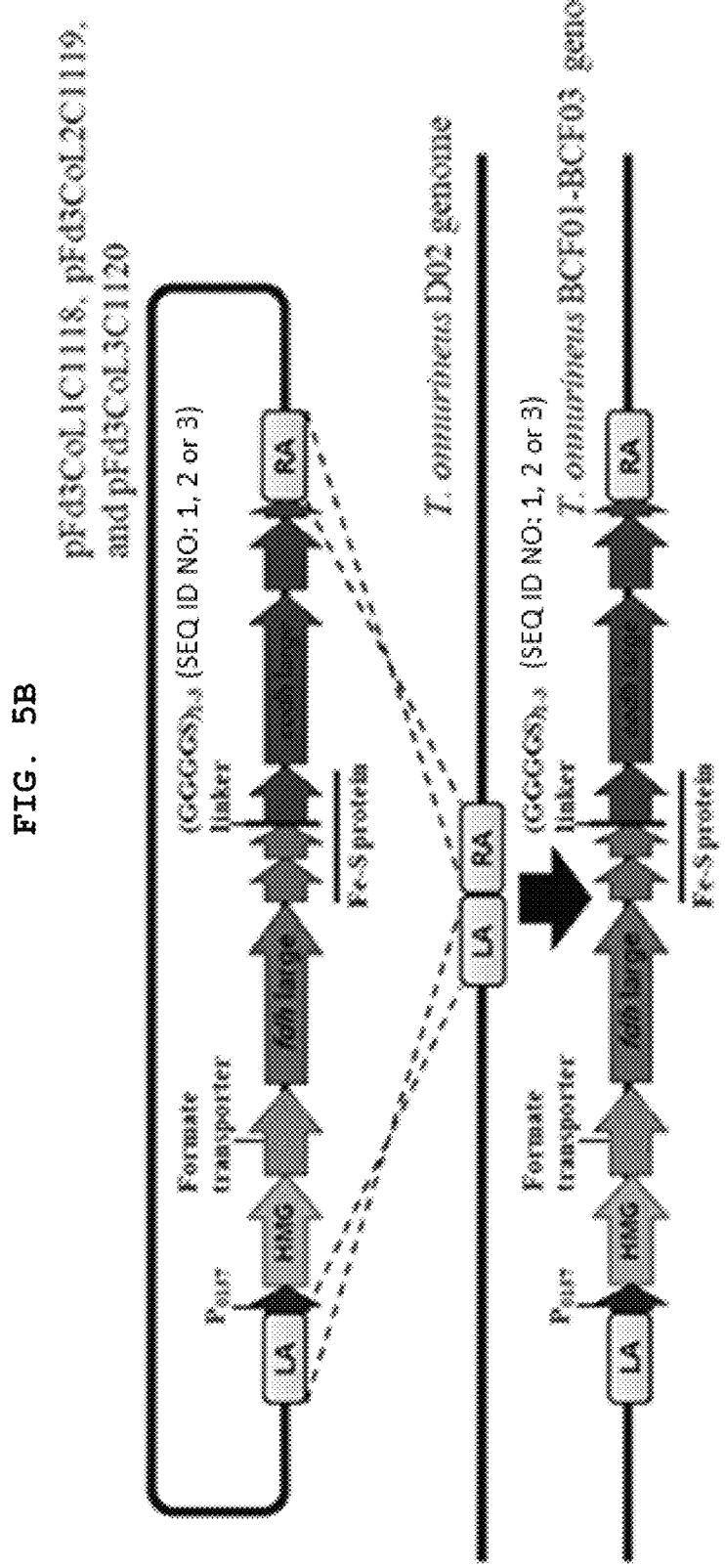
Figure 5C:
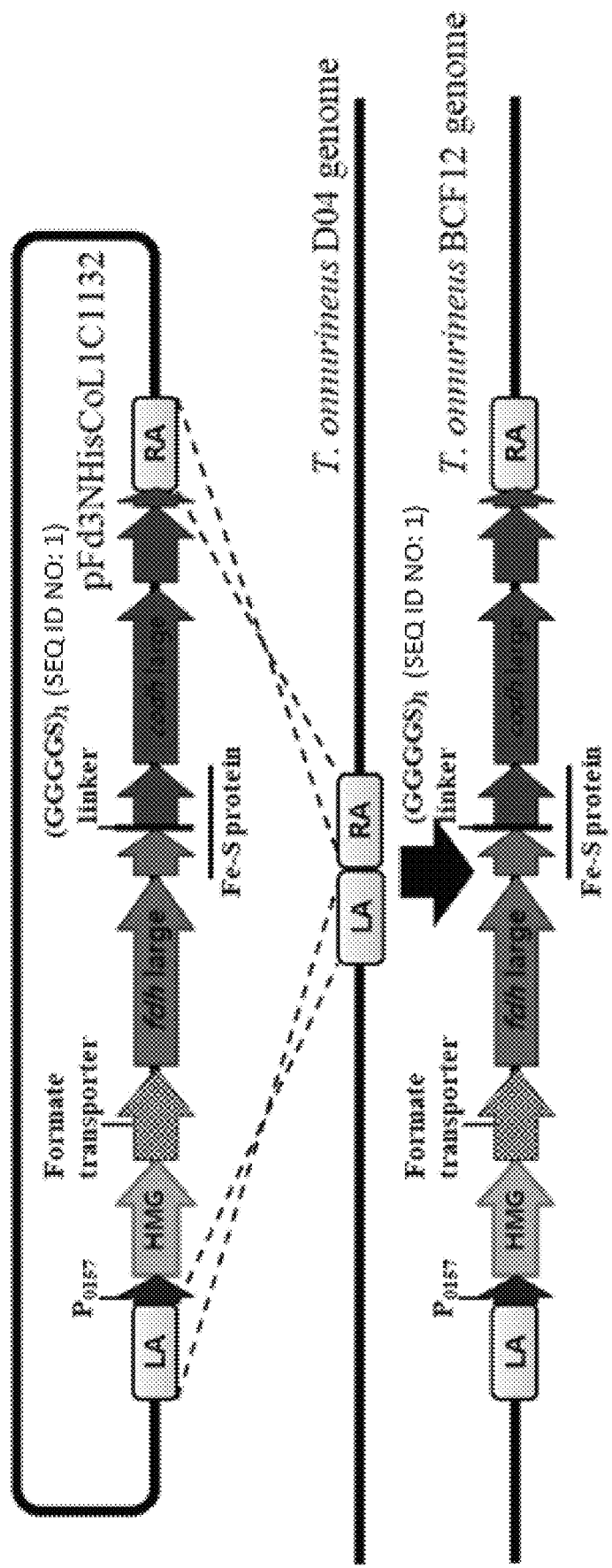

Hereinafter, the present invention will be described in more detail with reference to examples. These examples serve merely to illustrate the present invention, and thus the scope of the present invention is not construed as being limited by these examples.

Example 1. Cloning of Carbon Monoxide:Formate Oxidoreductase Fusion Protein

As an expression vector for a carbon monoxide:formate oxidoreductase (CFOR), pNA1comFosC1096 derived from the fosmid vector pCC1FOS was used.

pNA1comFosC1096 was constructed from pCC1FOS to have a 1-kb flanking region so that an insert DNA could be inserted between TON_1126 and TON_1127 of *Thermococcus onnurineus* NA1 used as a host cell.

The insert DNA was inserted together with the strong promoter $P_{0157}$ promoter and HMG-CoA reductase so as to have resistance to simvastatin.

The fdh3 region (TON_0539-0541) and codh region (TON_1017-1020) of *Thermococcus onnurineus* NA1 were amplified by PCR, and pFd3CoL1C1118, pFd3CoL2C1119 and pFd3CoL1C1120 recombinant plasmids were constructed so that the Fe—S proteins TON_0541 and TON_1017 were fused with each other by each of the linkers (GGGGS)$_1$ (SEQ ID NO: 1), (GGGGS)$_2$ (SEQ ID NO: 2) and (GGGGS)$_3$ (SEQ ID NO: 3). The recombinant plasmid pFd3NHisCoL1C1128 had the same structure as that of pFd3CoL1C1118, and His$_6$-tag was inserted into the N-terminus of Fdh3 so that isolation was possible by His-tag affinity chromatography.

The recombinant plasmid pFd3NHisCoL1C1132 was constructed to simplify the structure of CFOR and increase the efficiency of conversion of CO into formate. TON_0540 and TON_0541 of the fdh3 region are all Fe—S proteins that are subunits involved in electron transport. While the above-described plasmid was constructed so that TON_0541 and TON_1017 were fused to each other by the linker, pFd3NHisCoL1C1132 was constructed so that TON 0540 and TON_1017 were linked directly to each other. In addition, His$_6$-tag was inserted into the N-terminus of Fdh3 so that isolation of the CFOR protein was possible.

For construction of mutant strain D04, the fdh3 gene region was removed from the genome. To this end, the recombinant plasmid pldFdh3clusterA derived from a pUC118 vector was constructed. pldFdh3clusterA had the simvastatin-resistance gene HMG-CoA reductase as a selection marker, and a 1-kb region flanking the gene fdh3 region (TON 0539-0542) to be removed was inserted into each of the right arm (RA) and the left arm (LA). The primer sequences inserted into each recombinant plasmid are shown in Table 3 below.

TABLE 3

| Identifier | Sequence | Remarks |
| --- | --- | --- |
| priFCfosFdh3F | TAAAATGCTT GGGAGATGAC CTAGGATGGC ACAGAATAAT TCACTCG (SEQ ID NO: 18) | Forward primer used for PCR of fdh3 of BCF01, BCF02, BCF03 orBCFl2 |
| priFCfosFdh3R1 | GGCATGCTGC CTCCGCCGCC CCCCAGGTAA GCCTCATATT TG (SEQ ID NO: 19) | Linker-containing reverse primer used for PCR offdh3 of BCP01 |
| priFCfosFdh3R2 | GCTGCCTCCG CCGCCGCTTC CGCCTCCTCC CCCCAGGTAA GCCTCATATT TG (SEQ ID NO: 20) | Linker-containing reverse primer used for PCR of fdh3 of BCF02 |
| priFCfosFdh3R3 | GCTGGGCTGC CTCCGCCGCC CCCGAAGTAG GCGAGCG (SEQ ID NO: 21) | Linker-containing reverse primer used for PCR of fdh3 of BCF12 |
| priFCfosCodhFl | TGGGGGGCGG CGGAGGCAGC ATGCCAGCTT TTTCCGGTTC (SEQ ID NO: 22) | Linker-containing forward primer used for PCR of codh of BCFOl |
| priFCfosCodhF2 | GGCGGCGGAG GCAGCGGAGG AGGCGGAAGC ATGCCAGCTT TTTCCGGTTC (SEQ ID NO: 23) | Linker-containing forward primer used for PCR of codh of BCF02 |
| priFCfosCodhF3 | TCGGGGGCGG CGGAGGCAGC CCAGCTTTTT CCGGTTCC (SEQ ID NO: 24) | Linker-containing forward primer used for PCR of codh of BCF12 |
| priFCfosCodhR | TGGCCATCGT TGACGCCACG CATGCGACGT CTCACCTCCT GAGTTTAAAC CTCAT (SEQ ID NO: 25) | Reverse primer used for PCR of codh of BCF01, BCF02, BCF03 or BCF12 |
| priFd3NhisCoLaR | TCCTCGTGAT GGTGGTGATG GTGCATCCGC ACCACCGCCC T (SEQ ID NO: 26) | Left arm (LA) reverse primer used for insert DNA PCR of BCF09 and containing his-tag at N-terminus of Fdh3 |

TABLE 3-continued

| Identifier | Sequence | Remarks |
| --- | --- | --- |
| priFd3NhisCoRaF | GGATGCACCATCACCACCATCACGAGGAGTTTAAGATTGGCCTG(SEQ ID NO: 27) | Right arm (RA) reverse primer used for insert DNA PCR of BCF09 and containing his-tag at N-terminus of Fdh3 |
| priFd3ChisCoLaR | CTTCAGTGATGGTGGTGATGGTGGCACCCCCCAATCTTCTC(SEQ ID NO: 28) | Left arm (LA) reverse primer containing his-tag at C-terminus of Fdh3 |
| priFd3ChisCoRaF | GGTGCCACCATCACCACCATCACTGAAGATGGGAGAAAAAGCTGTTC(SEQ ID NO: 29) | Right arm (RA) reverse primer containing his-tag at C-terminus of Fdli3 |
| priFdSCoNhisLaR | CCGGCGTGATGGTGGTGATGGTGCATTTTCACCACCTCAATACCAC(SEQ ID NO: 30) | Left arm (LA) reverse primer containing his-tag at N-terminus of Codh |
| priFd3CoNhisRaF | AAATGCACCATCACCACCATCACGCCGGAAAGAAGGTTCCC(SEQ ID NO: 31) | Right arm (RA) reverse primer containing his-tag at N-terminus of Codh |
| priFd3CoChisLaR | TATTAGTGATGGTGGTGATGGTGGATGGGCCATCCAAGTCTTTTC(SEQ ID NO: 32) | Left arm (LA) reverse primer used for insert DNA PCR of BCF07 and containing his-tag at C-terminus of Codh |
| priFd3CoChisRaF | CCATCCACCATCACCACCATCACTAATAGTTTCTATTATTTAACTTTG(SEQ ID NO: 33) | Right (RA) reverse primer used for insert DNA PCR of BCF07 and containing his-tag at C-terminus of Codh |

Example 2. Construction of Mutant Strain

Mutant strain D01 of *Thermococcus onnurineus* is a mutant strain constructed by removing fdh2C (TON_1563-1564) and fdh3 (TON_0539) from the genome. Mutant strain D02 was constructed using D01 as a parent strain by removing fdh1C (TON_0280-0281) from the genome, and mutant strain D04 was constructed using D02 as a parent strain by removing fdh3C (TON_0539-0542)).

For transformation, *Thermococcus onnurineus* was pre-cultured in modified medium 1 (MM1) containing maltodextrin to obtain a culture of *Thermococcus onnurineus*. The culture was resuspended in 0.8× Artificial Sea Water (ASW), and then 5 µg of the recombinant plasmid of Example 1 was added thereto and introduced into the cells by heat shock at 80° C. Thereafter, a small amount of medium was added to the cells which were then stabilized at 80° C. for 2 hours. The stabilized transformed cells were inoculated and cultured in a medium containing 10 µM simvastatin, and passaged twice so as to be sufficiently enriched. Thereafter, a single colony was obtained and the genotype thereof was analyzed through PCR.

The mutant strains BCF01, BCF02 and BCF03 were constructed using D02 as a parent strain so that the fdh3 region (TON_0538-0541) and the codh region (TON_1017-1020) were fused with each other by each of the linkers $(GGGGS)_1$(SEQ ID NO: 1), $(GGGGS)_2$(SEQ ID NO: 2) and $(GGGGS)_3$(SEQ ID NO: 3).

The mutant strains BCF01, BCF02 and BCF03 were transformed with pFd3CoL1C1118, pFd3CoL2C1119 and pFd3CoL3C1120 recombinant plasmids, respectively, and the carbon monoxide:formate oxidoreductase (CFOR) introduced into each of the recombinant plasmids was inserted between TON_1126 and TON_1127 of *Thermococcus onnurineus*.

In addition, the mutant strain BCF09 was constructed using D02 as a parent strain and transformed with a pFd3NHisCoL1C1128 recombinant plasmid, and the same CFOR protein as in BCF01 was introduced therein. In addition, $His_6$-tag was added to the N-terminus of Fdh3.

In addition, the mutant strain BCF12 was constructed using D04 as a parent strain and transformed with a pFd3NHisCoL1C1132 recombinant plasmid so that the fdh3 region (TON_0538-0540) and the codh region (TON_1017-1020) were fused with each other by the linker $(GGGGS)_1$ (SEQ ID NO: 1). Also, $His_6$-tag was inserted into the N-terminus of Fdh3 (TON_0539).

The kinds of strains and plasmids used in the experiment are summarized in Table 4 below.

TABLE 4

Table 1. Strains and fosmids used this study.

| Strains or Plasmids | Description | Reference |
| --- | --- | --- |
| Strains | | |
| *E. coli* DH5a | Cloning host | TaKaRa |
| *T. onnurineus* | | |
| NA1 | Wild-type strain | Previous study |
| D01 | NA1 derivative, Δfdh2C ΔTON_0539 | Previous study |
| D02 | D01 derivative, Δfdh1C | Previous study |
| D04 | D02 derivative, Δfdh3C | This study |

TABLE 4-continued

Table 1. Strains and fosmids used this study.

| Strains or Plasmids | Description | Reference |
|---|---|---|
| BCF01 | D02 derivative, $P_{0157}hmg_{pfu}$::TON_0538-TON_0541:TON_1017-TON_1020; fusion of TON_0541 and TON_1017 with linker $(GGGGS)_1$ (SEQ ID NO: 1) | This study |
| BCF02 | D02 derivative, $P_{0157}hmg_{pfu}$::TON_0538-TON_0541:TON_1017-TON_1020; fusion of TON_0541 and TON_1017 with linker $(GGGGS)_2$ (SEQ ID NO: 2) | This study |
| BCF03 | D02 derivative, $P_{0157}hmg_{pfu}$::TON_0538-TON_0541:TON_1017-TON_1020; fusion of TON_0541 and TON_1017 with linker $(GGGGS)_3$ (SEQ ID NO: 3) | This study |
| BCF09 | D02 derivative, $P_{0157}hmg_{pfu}$::TON_0538-TON_0541:TON_1017-TON_1020; fusion of TON_0541 and TON_1017 with linker $(GGGGS)_1$ (SEQ ID NO: 1); $His_6$-tag inserted in N-terminus of Fdh3 (TON_0539) | This study |
| BCF12 | D04 derivative, $P_{0157}hmgpfu$::TON_0538-TON_0540:TON_1017-TON_1020; fusion of TON_0540 and TON_1017 with linker $(GGGGS)_1$ (SEQ ID NO: 1); $His_6$-tag inserted in N-terminus of Fdh3 (TON_0539) | This study |
| Fosmids | | |
| pCC1FOS | Backbone fosmid; $Cm^r$ | EPICENTRE |
| pNA1comFosC1096 | pCC1FOS carrying $P_{0157}$ promotor, HMG cassette, and 1 kbp Left-arm (LA) and Right-arm (RA) for homologous recombination of *T. onnurineus* NA1 genome; backbone fosmid for mutant construction; $Sim^r$ | This study |
| pFd3CoL1C1118 | pNA1comFosC1096 carrying fdh3 region (TON_0538-TON_0541) and codh region (TON_1017-TON_1020) from *T. onnurineus* NA1; fusion of TON_0541 and TON_1017 with linker $(GGGGS)_1$ (SEQ ID NO: 1) | This study |
| pFd3CoL2C1119 | pFd3CoL1C1118 carrying fusion of TON_0541 and TON_1017 with linker $(GGGGS)_2$ (SEQ ID NO: 2) | This study |
| pFd3CoL3C1120 | pFd3CoL1C1118 carrying fusion of TON_0541 and TON_1017 with linker $(GGGGS)_3$ (SEQ ID NO: 3) | This study |
| pFd3NHisCoL1C1128 | pFd3CoL1C1118 carrying fusion of TON_0541 and TON_1017 with linker $(GGGGS)_1$ (SEQ ID NO: 1); $His_6$-tag inserted in N-terminus of Fdh3 (TON_0539) | This study |
| pFd3NHisCoL1C1132 | pNA1comFosC1096 carrying fdh3 region (TON_0538-TON_0540) and codh region (TON_1017-TON_1020) from *T. onnurineus* NA1; fusion of TON_0540 and TON_1017 with linker $(GGGGS)_1$ (SEQ ID NO: 1); $His_6$-tag inserted in N-terminus of Fdh3 (TON_0539) | This study |

\* $Cm^r$, chloramphenicol resistance;
$Sim^r$, simvastatin resistance by HMG-CoA reductase;
fdh1C, fdh1-mfh1-mnh1 gene cluster (TON_0280-0281);
fdh2C, fdh2-mfh2-mnh2 gene cluster (TON_1563-1564);
fdh3C, fdh3 gene cluster (TON_0539-0542);
LA (left-arm) and RA (right-arm), 1 kbp DNA flanking region suitable for homologous recombination

Example 3. Culture of Transformant and Measurement of Formate Production

The transformant produced in Example 2 was cultured in modified medium 1 containing 4 g/L yeast extract, 35 g/L NaCl, 0.7 g/L KCl, 3.9 g/L $MgSO_4$, 0.4 g/L $CaCl_2 \cdot H_2O$, 0.3 g/L $NH_4Cl$, 0.15 g/L $Na_2HPO_4$, 0.03 g/L $NaSiO_3$, 0.5 g/L $NaHCO_3$, 0.5 g/L cysteine-HCl, 1 ml/L Holden's trace element, 2 ml/L Fe-EDTA solution, 1 ml/L Balch's vitamin solution, and 0.05 g/L $Na_3S \cdot 9H_2O$. The Fe-EDTA solution contained 1.54 g/L $FeSO_4 \cdot 9H_2O$ and 2.06 g/L $Na_2 \cdot EDTA$. The prepared medium was sterilized and then stored in an anaerobic chamber under anaerobic conditions. Each of the mutant strains D02, D04, BCF01, BCF02, BCF03 and BCF12 was cultured at 80° C. in a 160-ml serum vial containing 80 ml of medium and a head space filled with CO at 3 bar.

To measure the growth curve of each strain, the optical density was measured using a UV-Vis spectrophotometer (Shimadzu, UV-2600). The concentration of formate was analyzed using high-performance liquid chromatography (YL instrument, YL9100) with an ion exclusion chromatography column (Shodex, RSpak, KC-811) and measured using a UV detector. As a mobile phase, a 0.13 phosphoric acid aqueous solution was used. To analyze the gas composition of the final head space, gas chromatography (YL instrument, YL6100) with a Molsieve 5A column (Supelco, Bellefonte, PA) and a Porapack N column (Supelco) was used, and argon gas was used as a mobile phase.

Figure 6:
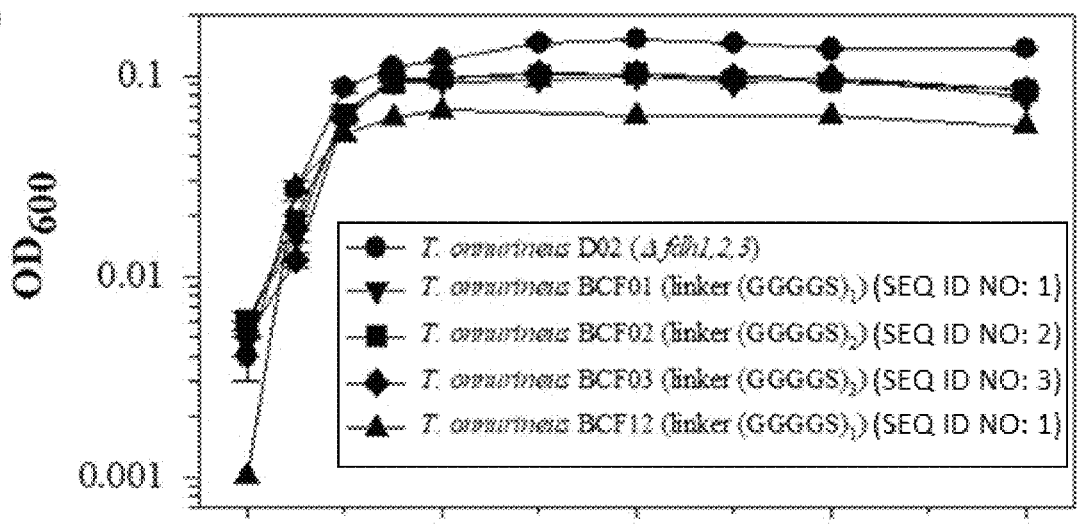
FIG. 6 depicts graphs showing the results of measuring changes in cell growth (A) and formate production (B) in transformants (*T. onnurineus* BCF01, BCF02, BCF03, and BCF12), into which the carbon monoxide:formate oxidoreductase (CFOR) has been introduced, under a CO condition.
Figure 6:
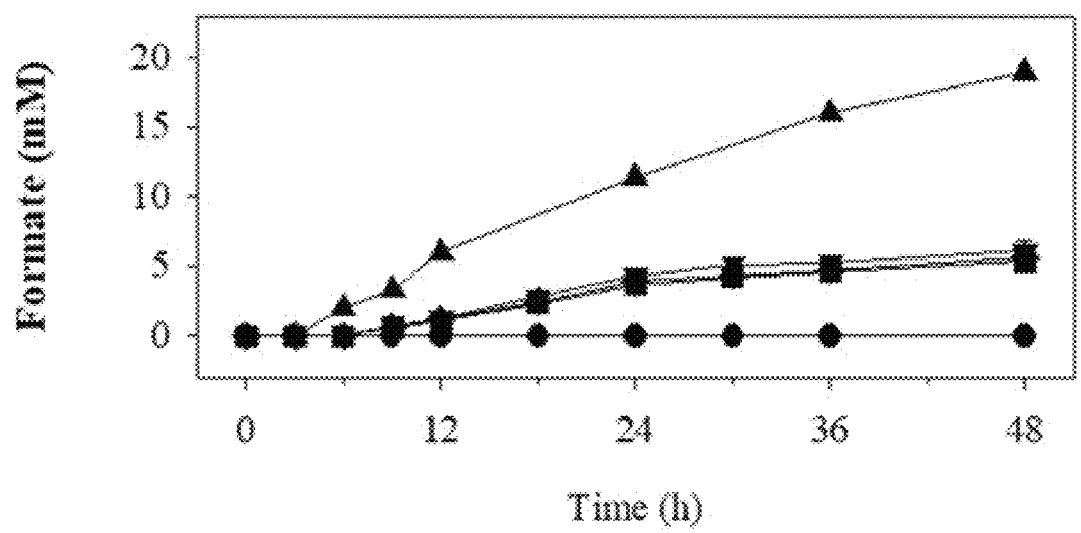
Figure 7:
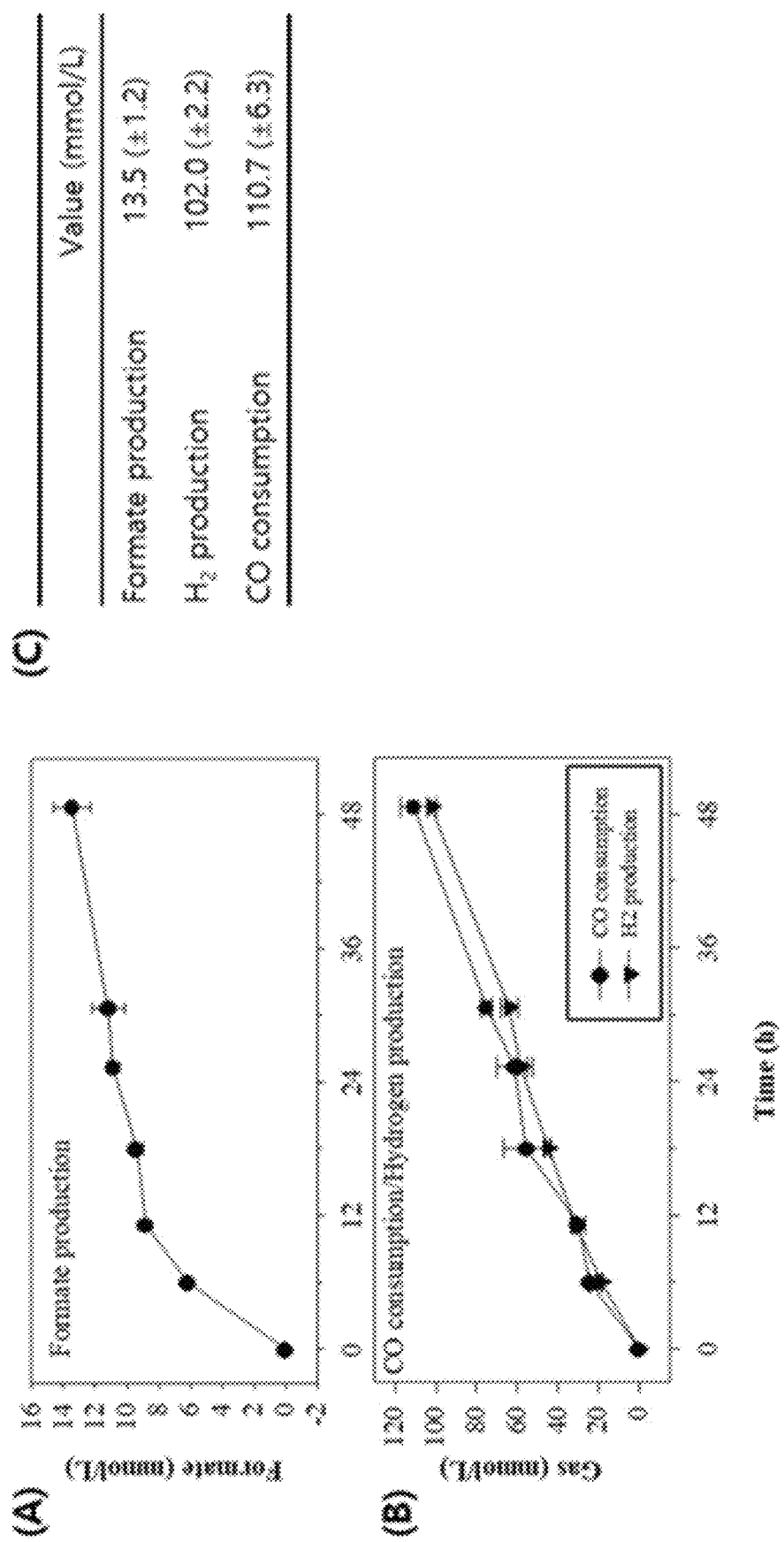
FIG. 7 depicts graphs showing the results of analyzing the CO gas-to-formate bioconversion performance of a *T. onnurineus* BCF12 strain through a resting cell experiment.

As a result, referring to FIG. 6, it was observed that the peak growth of the transformant including the recombinant plasmid introduced therein was inhibited at a relatively low level compared to the host strain *Thermococcus onnurineus* D02 strain ((A) of FIG. 6). In addition, it was confirmed that there was no formate production in the host strain *Thermococcus onnurineus* D02 strain, whereas formate was produced in all the BCF01, BCF02, BCF03 and BCF12 strains into which the recombinant plasmid was introduced ((B) of FIG. 6). From these results, it could be confirmed that electron transport was possible in the carbon monoxide: formate oxidoreductase (CFOR) of the present invention, synthesized to include the Fe—S fusion protein obtained by covalently linking two or more Fe—S proteins together through one to three 'GGGGS (SEQ ID NO: 1)' flexible linkers. In addition, it was confirmed that formate production in the BCF12 strain constructed using the (GGGGS)$_1$ (SEQ ID NO: 1) flexible linker was the highest (19 mM concentration).

Example 4. Analysis of CO Gas-to-Formate Bioconversion Performance Through Resting Cell Experiment A cell suspension to be used in a resting cell experiment was subjected to 5-L cell culture in a bioreactor. CO was continuously supplied, and the cells were harvested at an OD of 0.9 and centrifuged at 6,000 rpm for 30 minutes to isolate and harvest only the cells. A wash step of washing the obtained cells with an MM1 base (excluding yeast extract) free of nutrient components to remove components other than the cells was repeated three times. Finally, a resting cell experiment was performed using the cells with OD$_{600}$ of 0.5, suspended in an MM1 base.

In the resting cell experiment, 6 ml of the cell suspension with an OD$_{600}$ of 0.5 was placed in a 20-ml serum vial and then sealed, and the headspace was filled with 100% CO gas at a pressure of 2 bar, and then culture at 80° C. was performed. Formate production, CO consumption and hydrogen production were analyzed over time.

As a result, it could be confirmed that formate production continuously increased up to 48 hours, and CO gas consumption and hydrogen production were continuously maintained. As a result of stoichiometry at a time point of 48 hours, it could be confirmed that about 10, of CO consumption was converted to formate and about 90% was converted to bio-hydrogen.

Example 5. Isolation and Purification of Protein

All protein isolation and purification procedures were performed under anaerobic conditions. In order to determine at protein level whether CO was converted to formate, the isolation of the corresponding fusion protein from the nadFd3CoHisL1C1127 strain that is the CODH C-terminal his-tag strain including the carbon monoxide:formate oxidoreductase (CFOR) was performed using an affinity column purification method. The mutant strain nadFd3CoHisL1C1127 strain including the fusion protein was cultured 350 ml of MMC (bis-Tris pH 6.5) medium and inoculated into a bioreactor.

5-L cell culture was performed with the bioreactor. CO was continuously supplied, and the cells were harvested at an OD of 0.9 and centrifuged at 6,000 rpm for 30 minutes to harvest only the cells separately. The obtained cells were suspended well in talon buffer [50 mM Tris-HCl (pH 8.0), 0.1 M KCl, 10% glycerol], and then uniformly disrupted using a sonicator. Then, the carbon monoxide:formate oxidoreductase (CFOR) was isolated using a Talon affinity column.

Protein was isolated from talon resin using a talon buffer containing 300 mM imidazole, and the protein concentration was quantified by Bradford assay. The isolated and purified protein was analyzed by 121 SDS-PAGE.

Figure 8:
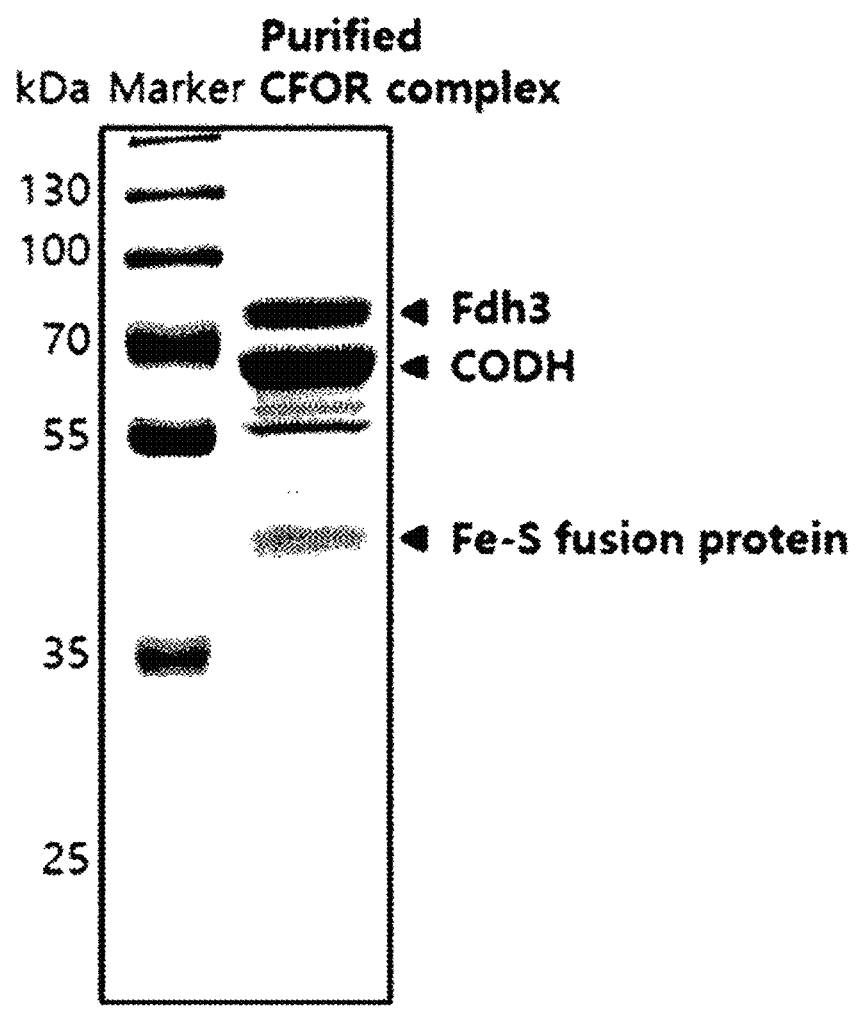
FIG. 8 is a photograph showing the results of PAGE of the carbon monoxide:formate oxidoreductase (CFOR) synthesized by the *T. onnurineus* BCF12 strain.

As a result, it could be observed that CO dehydrogenase (CODH) and formate dehydrogenase (Fdh) were isolated together with the TON_0540-TON_1017 protein which is the carbon monoxide:formate oxidoreductase (CFOR). From this result, it could be confirmed that CO dehydrogenase (CODH) and formate dehydrogenase (FDH3) were linked together by the Fe—S fusion protein to form a single new fusion protein (see FIG. 8).

Example 6. Measurement of Enzymatic Activities

The CODH enzyme activity, Fdh enzyme activity and CO gas-to-formate conversion ability of the carbon monoxide: formate oxidoreductase (CFOR) isolated in Example 5 were measured, and all experiments for measurement of the protein activities were measured under anaerobic conditions.

The CODH enzyme activity was measured using the methyl viologen method that quantifies the concentration of methyl viologen (MV) reduced when CO is given as an electron donor.

For activity measurement, 2 mM DTT, 10 mM MV and 0.5 μg CFOR protein were added to 1 ml of 50 mM Tris-HCl (pH 8.0) buffer in a cuvette sealed with a screw-cap, and then the cuvette was sealed by closing the lid. Then, the headspace was purged with CO gas and finally filled with CO gas at 1 bar, thus preparing a reaction.

The cuvette containing the mixture solution was placed on a heat block at 80° C., and the reaction was performed for 1 minute. Then, the reaction was terminated by placing the cuvette on ice, and the absorbance at a wavelength of 578 nm was measured using a spectrophotometer.

Measurement of the activity of formate dehydrogenase (FDH) was performed in the same manner as measurement of the CODH enzyme activity, except that 50 mM potassium phosphate (pH 7.6) buffer was used, formate was used instead of CO as an electron donor, and the enzymatic reaction was performed on a heat block at 80° C. for 5 minutes.

The activity of each of the CODH enzyme and the Fdh enzyme was calculated as the amount of enzyme catalyzing the reduction of 2 mmol methyl viologen, which is equivalent to the amount that catalyzes the oxidation of 1 mmol CO or formate. At this time, the extinction coefficient value is $\varepsilon_{578}=9.7$ mM$^{-1}$·cm$^{-1}$.

For measurement of the CO conversion/formate production activity of the isolated/purified fusion protein, 2 ml of a mixture solution obtained by adding the isolated fusion protein to each of five types of buffer (50 mM Bis-Tris pH 6.5, 150 mM HEPES pH 7.5, 50 mM potassium phosphate pH 7.6, 100 mM Tris pH 8.0, and 200 mM Bicine-KOH pH 8.5) at a final concentration of 100 μg/ml was tested in a 25-ml serum vial. A CO—CO$_2$ mixture gas (CO:CO$_2$=53.5: 46.5, vol./vol.) was injected into a 23-ml head space, and then reacted by incubation at 80° C. After 5 hours of the reaction, the concentration of formate produced was measured by LC.

Figure 9:
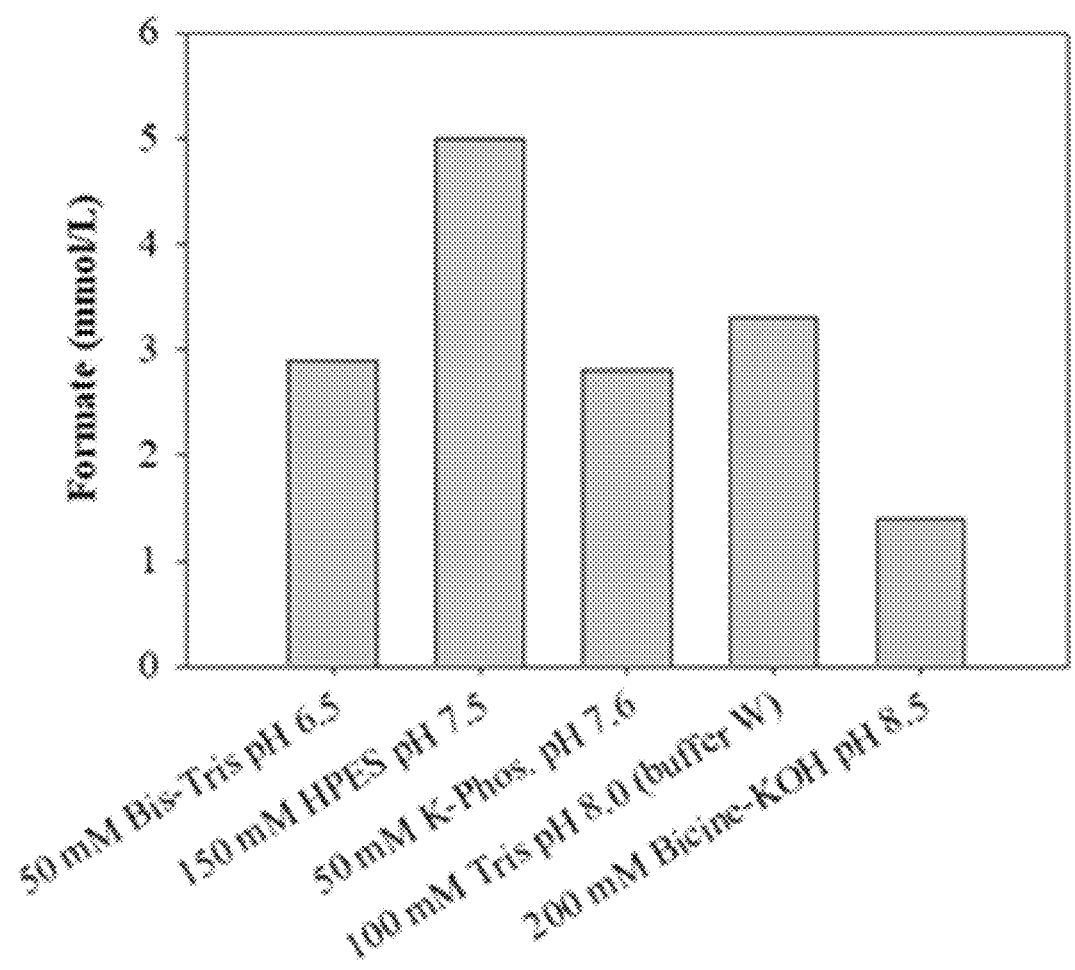
FIG. 9 is a graph showing the results of analyzing the CO gas-to-formate bioconversion enzyme activity of the carbon monoxide:formate oxidoreductase (CFOR) in different types of buffer.

As a result of measuring formate, formate production was found in all the buffer conditions, and the highest formate concentration (about 5 mmol/L) was measured in, 150 mM HEPES (pH 7.5). It was finally confirmed that formate was produced only from CO and CO gases under in vitro conditions (see FIG. 9).

TABLE 5

| Species | Specific activities (mmol min$^{-1}$ mg$^{-1}$) |
| --- | --- |
| CO dehydrogenase | 1.8 |
| Formate dehydrogenase | 120 |
| Formate production | 1.67 × 10$^{-4}$ |

From the above-described results, it could be finally confirmed that a new type of fusion protein consisting of a complex of CO dehydrogenase (CODH) and formate dehydrogenase (FDH) linked to each other through the Fe—S fusion protein acting as an electron transport chain was constructed, and the function of converting $CO_2$ to formate by the enzymatic reaction induced by electron transfer through the Fe—S proteins was actually achieved.

Example 7. Measurement of Formate Production Activity

Cells were inoculated into 1.5 L of MMC medium and then purged with 100; CO gas, and a batch culture bioreactor was operated at 80° C., and cell culture was performed under anaerobic conditions. A check valve was provided in a gas outlet to pressurize and regulate the gas pressure in the reactor.

Figure 10:
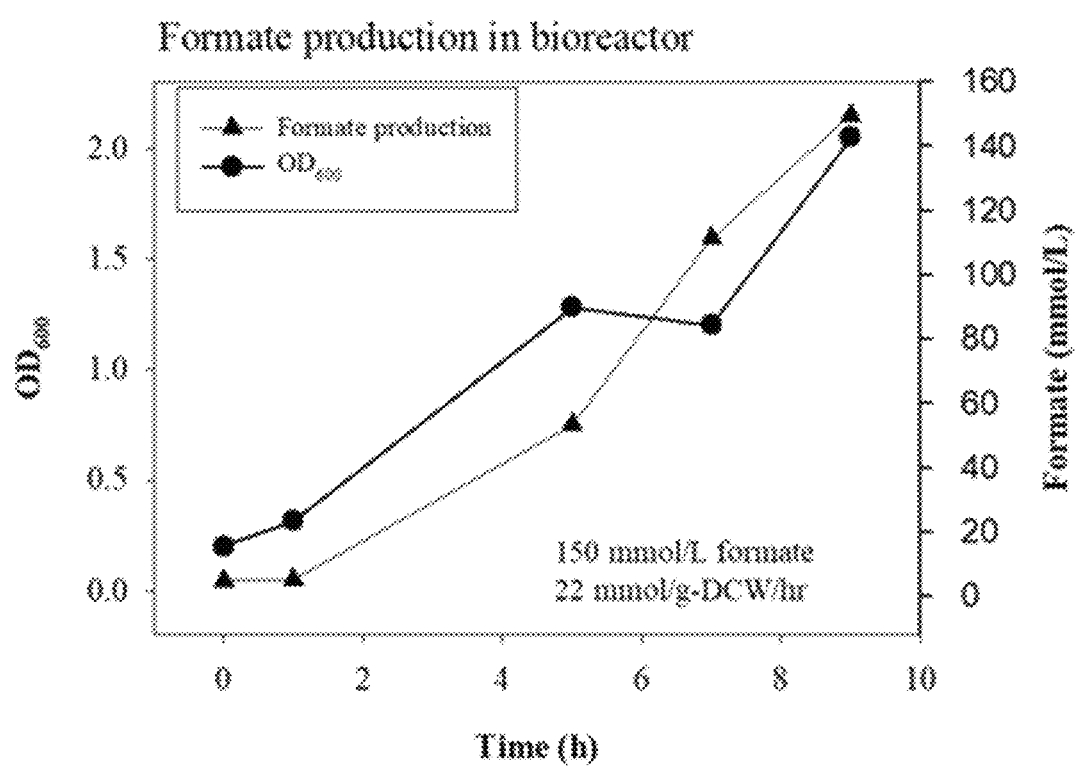
FIG. 10 is a graph showing the results of operating a bioreactor for the mutant strain *T. onnurineus* BCF12 strain into which the carbon monoxide:formate oxidoreductase (CFOR) has been introduced.

As a result of operating the bioreactor for 9 hours, it was confirmed that formate production was 150 mmol/L and specific formate production rate was 22 mmol/g-DCW/hr (see FIG. 10).

Although the present invention has been described in detail with reference to the specific features, it will be apparent to those skilled in the art that this description is only of a preferred embodiment thereof, and does not limit the scope of the present invention. Thus, the substantial scope of the present invention will be defined by the appended claims and equivalents thereto.

*Thermococcus* strain BCF12 strain was deposited in the Korea Research Institute of Bioscience and Biotechnology (having the address of 181, Ipsin-gil, Jeongeup-si, Jeollabuk-do 56212, Republic of Korea) under the Access number of KCTC 13649BP on Sep. 21, 2018. The deposit has been made under the terms of the Budapest Treaty and all restrictions imposed by the depositor on the availability to the public of the biological material will be irrevocably removed upon the granting of a patent.

What is claimed is:

1. An Fe—S fusion protein comprising:
a flexible linker having the amino acid sequence selected from the group consisting of SEQ ID NOs: 1 to 6; and
two or more Fe—S proteins, each comprising any one amino acid sequence selected from the group consisting of SEQ ID NOs: 7 to 11, the two or more Fe—S proteins covalently linked together through the flexible linker, the Fe—S fusion protein capable of acting as an electron transport chain functioning as a channel through which electrons move,
wherein the Fe—S fusion protein comprises the amino acid sequence of SEQ ID NO: 13.

2. The Fe—S fusion protein of claim 1, wherein the Fe—S fusion protein is formed by covalently linking two to five Fe—S proteins together through the flexible linker.

* * * * *

```
                          SEQUENCE LISTING

<160> NUMBER OF SEQ ID NOS: 33

<210> SEQ ID NO 1
<211> LENGTH: 5
<212> TYPE: PRT
<213> ORGANISM: Artificial Sequence
<220> FEATURE:
<223> OTHER INFORMATION: flexible linker of Fe-S Fusion Protein

<400> SEQUENCE: 1

Gly Gly Gly Gly Ser
1               5

<210> SEQ ID NO 2
<211> LENGTH: 10
<212> TYPE: PRT
<213> ORGANISM: Artificial Sequence
<220> FEATURE:
<223> OTHER INFORMATION: flexible linker of Fe-S Fusion Protein

<400> SEQUENCE: 2

Gly Gly Gly Gly Ser Gly Gly Gly Gly Ser
1               5                   10

<210> SEQ ID NO 3
<211> LENGTH: 15
<212> TYPE: PRT
<213> ORGANISM: Artificial Sequence
<220> FEATURE:
<223> OTHER INFORMATION: flexible linker of Fe-S Fusion Protein

<400> SEQUENCE: 3

Gly Gly Gly Gly Ser Gly Gly Gly Gly Ser Gly Gly Gly Gly Ser
1               5                   10                  15

<210> SEQ ID NO 4
<211> LENGTH: 20
<212> TYPE: PRT
<213> ORGANISM: Artificial Sequence
<220> FEATURE:
<223> OTHER INFORMATION: flexible linker of Fe-S Fusion Protein

<400> SEQUENCE: 4

Gly Gly Gly Gly Ser Gly Gly Gly Gly Ser Gly Gly Gly Gly Ser Gly
1               5                   10                  15
```

-continued

Gly Gly Gly Ser
            20

<210> SEQ ID NO 5
<211> LENGTH: 6
<212> TYPE: PRT
<213> ORGANISM: Artificial Sequence
<220> FEATURE:
<223> OTHER INFORMATION: flexible linker of Fe-S Fusion Protein

<400> SEQUENCE: 5

Gly Gly Gly Gly Gly Gly
1               5

<210> SEQ ID NO 6
<211> LENGTH: 8
<212> TYPE: PRT
<213> ORGANISM: Artificial Sequence
<220> FEATURE:
<223> OTHER INFORMATION: flexible linker of Fe-S Fusion Protein

<400> SEQUENCE: 6

Gly Gly Gly Gly Gly Gly Gly Gly
1               5

<210> SEQ ID NO 7
<211> LENGTH: 13
<212> TYPE: PRT
<213> ORGANISM: Artificial Sequence
<220> FEATURE:
<223> OTHER INFORMATION: cystein motif of Fe-S cluster
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(8)
<223> OTHER INFORMATION: Xaa can be any naturally occurring amino acid
<220> FEATURE:
<221> NAME/KEY: misc_feature
<222> LOCATION: (10)..(12)
<223> OTHER INFORMATION: Xaa can be any naturally occurring amino acid

<400> SEQUENCE: 7

Cys Xaa Xaa Cys Xaa Xaa Xaa Xaa Cys Xaa Xaa Xaa Cys
1               5                   10

<210> SEQ ID NO 8
<211> LENGTH: 11
<212> TYPE: PRT
<213> ORGANISM: Artificial Sequence
<220> FEATURE:
<223> OTHER INFORMATION: cystein motif of Fe-S cluster
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(10)
<223> OTHER INFORMATION: Xaa can be any naturally occurring amino acid

<400> SEQUENCE: 8

Cys Xaa Xaa Cys Xaa Xaa Cys Xaa Xaa Xaa Cys
1               5                   10

```
<210> SEQ ID NO 9
<211> LENGTH: 12
<212> TYPE: PRT
<213> ORGANISM: Artificial Sequence
<220> FEATURE:
<223> OTHER INFORMATION: cystein motif of Fe-S cluster
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(11)
<223> OTHER INFORMATION: Xaa can be any naturally occurring amino acid

<400> SEQUENCE: 9

Cys Xaa Xaa Cys Xaa Xaa Cys Xaa Xaa Xaa Xaa Cys
1               5                   10

<210> SEQ ID NO 10
<211> LENGTH: 4
<212> TYPE: PRT
<213> ORGANISM: Artificial Sequence
<220> FEATURE:
<223> OTHER INFORMATION: cystein motif of Fe-S cluster
<220> FEATURE:
<221> NAME/KEY: misc_feature
<222> LOCATION: (2)..(3)
<223> OTHER INFORMATION: Xaa can be any naturally occurring amino acid

<400> SEQUENCE: 10

Cys Xaa Xaa Cys
1

<210> SEQ ID NO 11
<211> LENGTH: 5
<212> TYPE: PRT
<213> ORGANISM: Artificial Sequence
<220> FEATURE:
<223> OTHER INFORMATION: cystein motif of Fe-S cluster
<220> FEATURE:
<221> NAME/KEY: misc_feature
<222> LOCATION: (2)..(4)
<223> OTHER INFORMATION: Xaa can be any naturally occurring amino acid

<400> SEQUENCE: 11

Cys Xaa Xaa Xaa Cys
1               5

<210> SEQ ID NO 12
<211> LENGTH: 630
<212> TYPE: PRT
<213> ORGANISM: Artificial Sequence
<220> FEATURE:
<223> OTHER INFORMATION: CO dehydrogenase part of Carbon
      Monoxide:Formate Oxidoreductase

<400> SEQUENCE: 12

Met Ala Gly Lys Lys Val Pro Ser Lys Gln Val Ser Ile Thr Pro Gly
1               5                   10                  15

Val Gly Lys Leu Ile Glu Lys Ala Glu Glu Asp Gly Val Lys Thr Ala
            20                  25                  30

Trp His Arg Phe Leu Glu Gln Gln Pro Gln Cys Gly Phe Gly Leu Leu
        35                  40                  45
```

```
Gly Val Cys Cys Lys Asn Cys Thr Met Gly Pro Cys Arg Ile Asp Pro
 50                  55                  60

Phe Gly Val Gly Pro Thr Lys Gly Val Cys Gly Ala Asp Ala Asp Thr
 65                  70                  75                  80

Ile Val Ala Arg Asn Ile Val Arg Met Ile Ala Ala Gly Thr Ala Gly
                 85                  90                  95

His Ser Asp His Ser Arg Asp Val Val His Val Phe Lys Gly Ile Ala
                100                 105                 110

Glu Gly Lys Phe Lys Asp Tyr Lys Leu Thr Asp Val Glu Lys Leu Lys
            115                 120                 125

Glu Leu Ala Lys Ile Leu Gly Val Thr Glu Gly Lys Ser Glu Asn
130                 135                 140

Glu Ile Ala Leu Glu Val Ala His Ile Leu Glu Met Glu Phe Gly Lys
145                 150                 155                 160

Gln Asp Glu Glu Pro Val Arg Leu Leu Ala Ala Thr Ala Pro Lys Lys
                165                 170                 175

Arg Ile Lys Val Trp Glu Lys Leu Gly Val Leu Pro Arg Ala Ile Asp
            180                 185                 190

Arg Glu Ile Cys Leu Ser Met His Arg Thr His Ile Gly Cys Asp Ala
            195                 200                 205

Asp Pro Ala Ser Leu Leu His Gly Val Arg Thr Ala Leu Ala Asp
    210                 215                 220

Gly Trp Cys Gly Ser Met Met Ala Thr Tyr Leu Ser Asp Ile Leu Phe
225                 230                 235                 240

Gly Thr Pro Lys Pro Ile Lys Ser Leu Ala Asn Leu Gly Val Leu Lys
                245                 250                 255

Glu Asp Met Val Asn Ile Ile Val His Gly His Asn Pro Ile Leu Ser
            260                 265                 270

Met Lys Ile Ala Glu Ile Ala Gln Ser Glu Met Gln Lys Leu Ala
            275                 280                 285

Glu Gln Tyr Gly Ala Lys Gly Ile Asn Val Ala Gly Met Cys Cys Thr
            290                 295                 300

Gly Asn Glu Val Leu Ser Arg Met Gly Val Gln Val Ala Gly Asn Phe
305                 310                 315                 320

Leu Met Gln Glu Leu Ala Ile Ile Thr Gly Ala Val Glu Ala Val Ile
                325                 330                 335

Val Asp Tyr Gln Cys Leu Met Pro Ser Leu Val Asp Val Ala Ser Cys
            340                 345                 350

Tyr His Thr Lys Ile Ile Thr Thr Glu Pro Lys Ala Arg Ile Pro Gly
            355                 360                 365

Ala Ile His Val Glu Phe Glu Pro Lys Ala Asp Glu Ile Ala Lys
    370                 375                 380

Glu Ile Ile Lys Ile Ala Ile Glu Asn Tyr Lys Asn Arg Val Pro Ala
385                 390                 395                 400

Lys Val Tyr Ile Pro Glu His Lys Met Glu Leu Val Ala Gly Phe Ser
                405                 410                 415

Val Glu Ala Ile Leu Glu Ala Leu Gly Gly Thr Leu Glu Pro Leu Ile
            420                 425                 430

Lys Ala Leu Gln Asp Gly Thr Ile Lys Gly Ile Val Gly Ile Val Gly
            435                 440                 445

Cys Asn Asn Pro Arg Val Lys Gln Asn Tyr Gly His Val Thr Leu Ala
450                 455                 460

Lys Glu Leu Ile Lys Arg Asp Ile Leu Val Val Gly Thr Gly Cys Trp
```

```
                    465                 470                 475                 480
        Gly Ile Ala Ala Ala Met His Gly Leu Leu Thr Pro Glu Ala Ala Glu
                            485                 490                 495

Met Ala Gly Pro Gly Leu Lys Ala Val Cys Glu Ala Leu Gly Ile Pro
                        500                 505                 510

Pro Cys Leu His Met Gly Ser Cys Val Asp Cys Ser Arg Ile Leu Leu
                        515                 520                 525

Val Leu Ser Ala Leu Ala Asn Ala Leu Asn Val Asp Ile Ser Asp Leu
                        530                 535                 540

Pro Val Ala Gly Ser Ala Pro Glu Trp Met Ser Glu Lys Ala Val Ala
        545                 550                 555                 560

Ile Gly Thr Tyr Phe Val Ala Ser Gly Val Phe Thr His Leu Gly Val
                            565                 570                 575

Ile Pro Pro Val Leu Gly Ser Gln Lys Val Thr Lys Leu Leu Thr Asp
                        580                 585                 590

Asp Ile Glu Asp Leu Leu Gly Gly Lys Phe Tyr Val Glu Thr Asp Pro
                        595                 600                 605

Val Lys Ala Ala Glu Thr Ile Tyr Asn Val Ile Glu Lys Arg Lys
                        610                 615                 620

Lys Leu Gly Trp Pro Ile
        625                 630

<210> SEQ ID NO 13
<211> LENGTH: 379
<212> TYPE: PRT
<213> ORGANISM: Artificial Sequence
<220> FEATURE:
<223> OTHER INFORMATION: Fe-S Fusion Protein

<400> SEQUENCE: 13

Met Glu Lys Lys Leu Phe Ile Asn Leu Gly Arg Cys Ile Ala Cys Arg
        1               5                   10                  15

Ala Cys Glu Val Ala Cys Glu Lys Glu His Gly Ile Ser Phe Ile Thr
                        20                  25                  30

Val Tyr Glu Phe Arg Asp Ile Ala Val Pro Leu Asn Cys Arg His Cys
                    35                  40                  45

Glu Lys Ala Pro Cys Ile Glu Val Cys Pro Thr Lys Ala Ile Tyr Arg
                50                  55                  60

Asp Glu Asp Gly Ala Val Val Ile Asp Glu Ser Lys Cys Ile Gly Cys
        65                  70                  75                  80

Tyr Met Cys Ser Ala Val Cys Pro Tyr Ala Ile Pro Ile Val Asp Pro
                        85                  90                  95

Ile Lys Glu Leu Ala Val Lys Cys Asp Leu Cys Ala Glu Arg Arg Lys
                    100                 105                 110

Glu Gly Arg Asp Pro Leu Cys Ala Ala Val Cys Pro Thr Asp Ala Ile
                115                 120                 125

Ile Tyr Ala Asp Leu Asn Glu Leu Met Glu Glu Lys Arg Arg Arg Lys
            130                 135                 140

Ala Glu Arg Ile Val Glu Ala Gln Arg Lys Ala Val Glu Thr Leu Ala
        145                 150                 155                 160

Tyr Phe Gly Gly Gly Gly Ser Pro Ala Phe Ser Gly Ser Asn Met
                        165                 170                 175

Glu Lys Leu Thr Ile Tyr Ile Asn Pro Glu Arg Cys Thr Gly Cys Arg
                    180                 185                 190

Ala Cys Glu Ile Ala Cys Ala Val Glu His Ser Met Ser Lys Asn Leu
```

```
                    195                 200                 205
Phe Gly Ala Ile Phe Glu Lys Pro Thr Pro Lys Pro Arg Leu Gln Val
210                 215                 220

Val Val Ala Asp Phe Phe Asn Val Pro Met Arg Cys Gln His Cys Glu
225                 230                 235                 240

Asp Ala Pro Cys Met Glu Ala Cys Pro Thr Gly Ala Ile Ser Arg Thr
                245                 250                 255

Lys Glu Gly Phe Val Val Leu Asn Ala Asn Lys Cys Ile Gly Cys Leu
                260                 265                 270

Met Cys Val Met Ala Cys Pro Phe Gly His Pro Lys Phe Glu Pro Glu
                275                 280                 285

Tyr Lys Ala Val Ile Lys Cys Asp Ser Cys Val Asp Arg Val Arg Glu
                290                 295                 300

Gly Lys Glu Pro Ala Cys Val Glu Ala Cys Pro Thr Arg Ala Leu Lys
305                 310                 315                 320

Phe Gly Thr Leu Gly Glu Ile Leu Glu Glu Val Arg Lys Glu Lys Ala
                325                 330                 335

Glu Ser Leu Ile Ser Gly Leu Lys Ser Gln Gly Met Val Tyr Met Lys
                340                 345                 350

Pro Val Ser Glu Ser Lys Lys Lys Glu Asp Leu Val Arg Pro Met Asp
                355                 360                 365

Leu Tyr Leu Ala Tyr Ser Asn Val Val Trp Tyr
370                 375
```

<210> SEQ ID NO 14
<211> LENGTH: 680
<212> TYPE: PRT
<213> ORGANISM: Artificial Sequence
<220> FEATURE:
<223> OTHER INFORMATION: Fomrate dehydrogenase

<400> SEQUENCE: 14

```
Met Glu Glu Phe Lys Ile Gly Leu Cys Pro Tyr Cys Gly Met Gly Cys
1               5                   10                  15

Arg Phe Tyr Ile Lys Thr Leu Asn Gly Gln Pro Ile Gly Ile Glu Pro
                20                  25                  30

Tyr Pro Gly Gly Val Asn Glu Gly Lys Leu Cys Pro Lys Gly Val Ala
                35                  40                  45

Ala Val Asp Phe Leu Arg His Lys Asp Arg Leu Lys Lys Pro Leu Lys
                50                  55                  60

Arg Thr Glu Asn Gly Phe Val Glu Ile Ser Trp Glu Gln Ala Ile Lys
65                  70                  75                  80

Glu Ile Ala Glu Lys Leu Leu Glu Ile Arg Glu Lys Tyr Gly Pro Asp
                85                  90                  95

Thr Leu Gly Phe Phe Ser Ser Ala Arg Cys Ser Asn Glu Glu Asn Tyr
                100                 105                 110

Leu Leu Gln Lys Ile Ala Arg Leu Leu Gly Thr Asn Asn Val Asp His
                115                 120                 125

Cys Ala Arg Leu Cys His Ala Ser Thr Val Val Gly Leu Ala Gln Thr
                130                 135                 140

Val Gly Ala Ala Ala Gln Ser Gly Ser Tyr Thr Asp Ile Pro Lys Ala
145                 150                 155                 160

Lys Val Leu Leu Ile Trp Gly Tyr Asn Pro Ser Glu Thr His Pro Val
                165                 170                 175

Leu Met Arg Tyr Ile Leu Arg Ala Arg Asp Asn Gly Ala Lys Ile Ile
```

```
            180                 185                 190
Val Val Asp Pro Arg Lys Thr Arg Thr Val Trp Phe Ala Asp Met His
            195                 200                 205
Leu Gln Leu Lys Pro Gly Thr Asp Ile Val Leu Ala Asn Ala Met Met
            210                 215                 220
His Val Ile Ile Glu Glu Arg Leu Tyr Asp Arg Glu Phe Ile Met Asn
225                 230                 235                 240
Arg Thr Lys Gly Phe Glu Lys Leu Ile Ala Ala Val Gln Lys Tyr Thr
                245                 250                 255
Pro Glu Tyr Ala Glu Glu Ile Thr Gly Val Pro Ala Lys Leu Ile Arg
                260                 265                 270
Glu Ala Ala Ile Thr Phe Ala Thr Ala Gly Arg Gly Ile Val Met Trp
            275                 280                 285
Ala Met Gly Leu Thr Gln His Val Thr Gly Ala Ala Asn Val Lys Ala
            290                 295                 300
Leu Ala Asp Leu Ala Leu Ile Cys Gly Tyr Val Gly Arg Glu Gly Thr
305                 310                 315                 320
Gly Leu Phe Pro Met Arg Gly Gln Asn Asn Val Gln Gly Ala Cys Asp
                325                 330                 335
Met Ala Ala Leu Pro Asn Val Phe Pro Gly Tyr Gln Lys Val Thr Asp
                340                 345                 350
Asp Glu Lys Arg Lys His Val Ala Glu Ile Trp Gly Val Glu Asp Leu
                355                 360                 365
Pro Ser Lys Pro Gly Leu Thr Ile Pro Glu Met Ile Asp Ala Ala Ala
            370                 375                 380
Lys Gly Glu Leu Lys Ala Leu Tyr Ile Met Gly Glu Asn Pro Val Met
385                 390                 395                 400
Ser Asp Pro Asn Thr Lys His Val Ile Glu Ala Leu Lys Asn Leu Glu
                405                 410                 415
Leu Leu Val Val Gln Asp Ile Phe Leu Thr Glu Thr Ala Glu Leu Ala
                420                 425                 430
His Tyr Val Leu Pro Ala Ala Ala Tyr Ala Glu Lys Glu Gly Ser Phe
            435                 440                 445
Thr Ala Ser Glu Arg Arg Val Gln Trp Asn Phe Lys Ala Ile Glu Pro
            450                 455                 460
Pro Gly Glu Ala Lys Pro Asp Trp Glu Ile Leu Thr Met Leu Gly Lys
465                 470                 475                 480
Ala Leu Gly Leu Pro Lys Phe Asp Tyr Ser Asp Val Glu Asp Ile Thr
                485                 490                 495
Arg Glu Ile Thr Leu Val Ala Pro Gln Tyr Arg Gly Ile Thr Pro Glu
                500                 505                 510
Arg Leu Lys Arg Glu Val Met Gly Val Gln Trp Pro Cys Pro Ser Glu
                515                 520                 525
Asp His Pro Gly Thr Pro Arg Leu His Val Glu Arg Phe Ala Thr Pro
            530                 535                 540
Asp Gly Lys Ala Asn Ile Ile Pro Val Glu Phe Lys Pro Pro Ala Glu
545                 550                 555                 560
Glu Pro Asp Glu Glu Tyr Pro Phe Ile Leu Thr Thr Phe Arg Ile Val
                565                 570                 575
Gly Gln Tyr His Thr Leu Thr Met Ser Asn Arg Ser Glu Ser Leu Lys
                580                 585                 590
Lys Arg Trp Ser Ser Pro Tyr Ala Gln Ile Ser Pro Glu Asp Ala Lys
            595                 600                 605
```

```
Lys Leu Gly Ile Gln Asp Gly Glu Met Ile Arg Ile Val Thr Arg Arg
        610                 615                 620

Gly Ser Tyr Thr Cys Arg Ala Val Val Thr Glu Asp Val Ser Glu Gly
625                 630                 635                 640

Val Ile Ala Val Pro Trp His Trp Gly Ala Asn Ile Leu Thr Asn Asp
                645                 650                 655

Val Leu Asp Pro Glu Ala Lys Ile Pro Glu Leu Lys Val Ala Ala Cys
                660                 665                 670

Arg Val Glu Lys Ile Gly Gly Cys
        675                 680

<210> SEQ ID NO 15
<211> LENGTH: 1689
<212> TYPE: PRT
<213> ORGANISM: Artificial Sequence
<220> FEATURE:
<223> OTHER INFORMATION: Noble Carbon Monoxide:Formate Oxidoreductase

<400> SEQUENCE: 15

Met Ala Gly Lys Lys Val Pro Ser Lys Gln Val Ser Ile Thr Pro Gly
1               5                   10                  15

Val Gly Lys Leu Ile Glu Lys Ala Glu Glu Asp Gly Val Lys Thr Ala
                20                  25                  30

Trp His Arg Phe Leu Gln Gln Pro Gln Cys Gly Phe Gly Leu Leu
                35                  40                  45

Gly Val Cys Cys Lys Asn Cys Thr Met Gly Pro Cys Arg Ile Asp Pro
        50                  55                  60

Phe Gly Val Gly Pro Thr Lys Gly Val Cys Gly Ala Asp Ala Asp Thr
65                  70                  75                  80

Ile Val Ala Arg Asn Ile Val Arg Met Ile Ala Ala Gly Thr Ala Gly
                85                  90                  95

His Ser Asp His Ser Arg Asp Val Val His Val Phe Lys Gly Ile Ala
                100                 105                 110

Glu Gly Lys Phe Lys Asp Tyr Lys Leu Thr Asp Val Glu Lys Leu Lys
            115                 120                 125

Glu Leu Ala Lys Ile Leu Gly Val Glu Thr Glu Gly Lys Ser Glu Asn
        130                 135                 140

Glu Ile Ala Leu Glu Val Ala His Ile Leu Glu Met Glu Phe Gly Lys
145                 150                 155                 160

Gln Asp Glu Glu Pro Val Arg Leu Leu Ala Ala Thr Ala Pro Lys Lys
                165                 170                 175

Arg Ile Lys Val Trp Glu Lys Leu Gly Val Leu Pro Arg Ala Ile Asp
                180                 185                 190

Arg Glu Ile Cys Leu Ser Met His Arg Thr His Ile Gly Cys Asp Ala
            195                 200                 205

Asp Pro Ala Ser Leu Leu Leu His Gly Val Arg Thr Ala Leu Ala Asp
        210                 215                 220

Gly Trp Cys Gly Ser Met Met Ala Thr Tyr Leu Ser Asp Ile Leu Phe
225                 230                 235                 240

Gly Thr Pro Lys Pro Ile Lys Ser Leu Ala Asn Leu Gly Val Leu Lys
                245                 250                 255

Glu Asp Met Val Asn Ile Ile Val His Gly His Asn Pro Ile Leu Ser
                260                 265                 270

Met Lys Ile Ala Glu Ile Ala Gln Ser Glu Glu Met Gln Lys Leu Ala
            275                 280                 285
```

```
Glu Gln Tyr Gly Ala Lys Gly Ile Asn Val Ala Gly Met Cys Cys Thr
    290                 295                 300
Gly Asn Glu Val Leu Ser Arg Met Gly Val Gln Val Ala Gly Asn Phe
305                 310                 315                 320
Leu Met Gln Glu Leu Ala Ile Ile Thr Gly Ala Val Glu Ala Val Ile
                325                 330                 335
Val Asp Tyr Gln Cys Leu Met Pro Ser Leu Val Asp Val Ala Ser Cys
            340                 345                 350
Tyr His Thr Lys Ile Ile Thr Thr Glu Pro Lys Ala Arg Ile Pro Gly
        355                 360                 365
Ala Ile His Val Glu Phe Glu Pro Glu Lys Ala Asp Glu Ile Ala Lys
    370                 375                 380
Glu Ile Ile Lys Ile Ala Ile Glu Asn Tyr Lys Asn Arg Val Pro Ala
385                 390                 395                 400
Lys Val Tyr Ile Pro Glu His Lys Met Glu Leu Val Ala Gly Phe Ser
                405                 410                 415
Val Glu Ala Ile Leu Glu Ala Leu Gly Gly Thr Leu Glu Pro Leu Ile
            420                 425                 430
Lys Ala Leu Gln Asp Gly Thr Ile Lys Gly Ile Val Gly Ile Val Gly
        435                 440                 445
Cys Asn Asn Pro Arg Val Lys Gln Asn Tyr Gly His Val Thr Leu Ala
    450                 455                 460
Lys Glu Leu Ile Lys Arg Asp Ile Leu Val Val Gly Thr Gly Cys Trp
465                 470                 475                 480
Gly Ile Ala Ala Ala Met His Gly Leu Leu Thr Pro Glu Ala Ala Glu
                485                 490                 495
Met Ala Gly Pro Gly Leu Lys Ala Val Cys Glu Ala Leu Gly Ile Pro
            500                 505                 510
Pro Cys Leu His Met Gly Ser Cys Val Asp Cys Ser Arg Ile Leu Leu
        515                 520                 525
Val Leu Ser Ala Leu Ala Asn Ala Leu Asn Val Asp Ile Ser Asp Leu
    530                 535                 540
Pro Val Ala Gly Ser Ala Pro Glu Trp Met Ser Glu Lys Ala Val Ala
545                 550                 555                 560
Ile Gly Thr Tyr Phe Val Ala Ser Gly Val Phe Thr His Leu Gly Val
                565                 570                 575
Ile Pro Pro Val Leu Gly Ser Gln Lys Val Thr Lys Leu Leu Thr Asp
            580                 585                 590
Asp Ile Glu Asp Leu Leu Gly Gly Lys Phe Tyr Val Glu Thr Asp Pro
        595                 600                 605
Val Lys Ala Ala Glu Thr Ile Tyr Asn Val Ile Glu Lys Arg Lys
    610                 615                 620
Lys Leu Gly Trp Pro Ile Met Glu Lys Leu Phe Ile Asn Leu Gly
625                 630                 635                 640
Arg Cys Ile Ala Cys Arg Ala Cys Glu Val Ala Cys Glu Lys Glu His
                645                 650                 655
Gly Ile Ser Phe Ile Thr Val Tyr Glu Phe Arg Asp Ile Ala Val Pro
            660                 665                 670
Leu Asn Cys Arg His Cys Glu Lys Ala Pro Cys Ile Glu Val Cys Pro
        675                 680                 685
Thr Lys Ala Ile Tyr Arg Asp Glu Asp Gly Ala Val Val Ile Asp Glu
    690                 695                 700
```

-continued

Ser Lys Cys Ile Gly Cys Tyr Met Cys Ser Ala Val Cys Pro Tyr Ala
705                 710                 715                 720

Ile Pro Ile Val Asp Pro Ile Lys Glu Leu Ala Val Lys Cys Asp Leu
            725                 730                 735

Cys Ala Glu Arg Arg Lys Glu Gly Arg Asp Pro Leu Cys Ala Ala Val
            740                 745                 750

Cys Pro Thr Asp Ala Ile Ile Tyr Ala Asp Leu Asn Glu Leu Met Glu
            755                 760                 765

Glu Lys Arg Arg Arg Lys Ala Glu Arg Ile Val Glu Ala Gln Arg Lys
    770                 775                 780

Ala Val Glu Thr Leu Ala Tyr Phe Gly Gly Gly Gly Ser Pro Ala
785                 790                 795                 800

Phe Ser Gly Ser Asn Met Glu Lys Leu Thr Ile Tyr Ile Asn Pro Glu
                805                 810                 815

Arg Cys Thr Gly Cys Arg Ala Cys Glu Ile Ala Cys Ala Val Glu His
                820                 825                 830

Ser Met Ser Lys Asn Leu Phe Gly Ala Ile Phe Glu Lys Pro Thr Pro
                835                 840                 845

Lys Pro Arg Leu Gln Val Val Ala Asp Phe Phe Asn Val Pro Met
850                 855                 860

Arg Cys Gln His Cys Glu Asp Ala Pro Cys Met Glu Ala Cys Pro Thr
865                 870                 875                 880

Gly Ala Ile Ser Arg Thr Lys Glu Gly Phe Val Val Leu Asn Ala Asn
                885                 890                 895

Lys Cys Ile Gly Cys Leu Met Cys Val Met Ala Cys Pro Phe Gly His
                900                 905                 910

Pro Lys Phe Glu Pro Glu Tyr Lys Ala Val Ile Lys Cys Asp Ser Cys
        915                 920                 925

Val Asp Arg Val Arg Glu Gly Lys Glu Pro Ala Cys Val Glu Ala Cys
    930                 935                 940

Pro Thr Arg Ala Leu Lys Phe Gly Thr Leu Gly Glu Ile Leu Glu Glu
945                 950                 955                 960

Val Arg Lys Glu Lys Ala Glu Ser Leu Ile Ser Gly Leu Lys Ser Gln
                965                 970                 975

Gly Met Val Tyr Met Lys Pro Val Ser Glu Ser Lys Lys Lys Glu Asp
                980                 985                 990

Leu Val Arg Pro Met Asp Leu Tyr Leu Ala Tyr Ser Asn Val Val Trp
        995                 1000                1005

Tyr Met Glu Glu Phe Lys Ile Gly Leu Cys Pro Tyr Cys Gly Met
    1010                1015                1020

Gly Cys Arg Phe Tyr Ile Lys Thr Leu Asn Gly Gln Pro Ile Gly
    1025                1030                1035

Ile Glu Pro Tyr Pro Gly Gly Val Asn Glu Gly Lys Leu Cys Pro
    1040                1045                1050

Lys Gly Val Ala Ala Val Asp Phe Leu Arg His Lys Asp Arg Leu
    1055                1060                1065

Lys Lys Pro Leu Lys Arg Thr Glu Asn Gly Phe Val Glu Ile Ser
    1070                1075                1080

Trp Glu Gln Ala Ile Lys Glu Ile Ala Glu Lys Leu Leu Glu Ile
    1085                1090                1095

Arg Glu Lys Tyr Gly Pro Asp Thr Leu Gly Phe Phe Ser Ser Ala
    1100                1105                1110

Arg Cys Ser Asn Glu Glu Asn Tyr Leu Leu Gln Lys Ile Ala Arg

-continued

```
              1115                1120                1125
Leu Leu Gly Thr Asn Asn Val Asp His Cys Ala Arg Leu Cys His
    1130                1135                1140
Ala Ser Thr Val Val Gly Leu Ala Gln Thr Val Gly Ala Ala Ala
    1145                1150                1155
Gln Ser Gly Ser Tyr Thr Asp Ile Pro Lys Ala Lys Val Leu Leu
    1160                1165                1170
Ile Trp Gly Tyr Asn Pro Ser Glu Thr His Pro Val Leu Met Arg
    1175                1180                1185
Tyr Ile Leu Arg Ala Arg Asp Asn Gly Ala Lys Ile Ile Val Val
    1190                1195                1200
Asp Pro Arg Lys Thr Arg Thr Val Trp Phe Ala Asp Met His Leu
    1205                1210                1215
Gln Leu Lys Pro Gly Thr Asp Ile Val Leu Ala Asn Ala Met Met
    1220                1225                1230
His Val Ile Ile Glu Glu Arg Leu Tyr Asp Arg Glu Phe Ile Met
    1235                1240                1245
Asn Arg Thr Lys Gly Phe Glu Lys Leu Ile Ala Ala Val Gln Lys
    1250                1255                1260
Tyr Thr Pro Glu Tyr Ala Glu Glu Ile Thr Gly Val Pro Ala Lys
    1265                1270                1275
Leu Ile Arg Glu Ala Ala Ile Thr Phe Ala Thr Ala Gly Arg Gly
    1280                1285                1290
Ile Val Met Trp Ala Met Gly Leu Thr Gln His Val Thr Gly Ala
    1295                1300                1305
Ala Asn Val Lys Ala Leu Ala Asp Leu Ala Leu Ile Cys Gly Tyr
    1310                1315                1320
Val Gly Arg Glu Gly Thr Gly Leu Phe Pro Met Arg Gly Gln Asn
    1325                1330                1335
Asn Val Gln Gly Ala Cys Asp Met Ala Ala Leu Pro Asn Val Phe
    1340                1345                1350
Pro Gly Tyr Gln Lys Val Thr Asp Asp Glu Lys Arg Lys His Val
    1355                1360                1365
Ala Glu Ile Trp Gly Val Glu Asp Leu Pro Ser Lys Pro Gly Leu
    1370                1375                1380
Thr Ile Pro Glu Met Ile Asp Ala Ala Lys Gly Glu Leu Lys
    1385                1390                1395
Ala Leu Tyr Ile Met Gly Glu Asn Pro Val Met Ser Asp Pro Asn
    1400                1405                1410
Thr Lys His Val Ile Glu Ala Leu Lys Asn Leu Glu Leu Leu Val
    1415                1420                1425
Val Gln Asp Ile Phe Leu Thr Glu Thr Ala Glu Leu Ala His Tyr
    1430                1435                1440
Val Leu Pro Ala Ala Ala Tyr Ala Glu Lys Glu Gly Ser Phe Thr
    1445                1450                1455
Ala Ser Glu Arg Arg Val Gln Trp Asn Phe Lys Ala Ile Glu Pro
    1460                1465                1470
Pro Gly Glu Ala Lys Pro Asp Trp Glu Ile Leu Thr Met Leu Gly
    1475                1480                1485
Lys Ala Leu Gly Leu Pro Lys Phe Asp Tyr Ser Asp Val Glu Asp
    1490                1495                1500
Ile Thr Arg Glu Ile Thr Leu Val Ala Pro Gln Tyr Arg Gly Ile
    1505                1510                1515
```

| Thr | Pro | Glu | Arg | Leu | Lys | Arg | Glu | Val | Met | Gly | Val | Gln | Trp | Pro |
|  | 1520 |  |  |  | 1525 |  |  |  | 1530 |  |  |  |  |  |

| Cys | Pro | Ser | Glu | Asp | His | Pro | Gly | Thr | Pro | Arg | Leu | His | Val | Glu |
| 1535 |  |  |  |  | 1540 |  |  |  |  | 1545 |  |  |  |  |

| Arg | Phe | Ala | Thr | Pro | Asp | Gly | Lys | Ala | Asn | Ile | Ile | Pro | Val | Glu |
| 1550 |  |  |  |  | 1555 |  |  |  |  | 1560 |  |  |  |  |

| Phe | Lys | Pro | Pro | Ala | Glu | Glu | Pro | Asp | Glu | Glu | Tyr | Pro | Phe | Ile |
| 1565 |  |  |  |  | 1570 |  |  |  |  | 1575 |  |  |  |  |

| Leu | Thr | Thr | Phe | Arg | Ile | Val | Gly | Gln | Tyr | His | Thr | Leu | Thr | Met |
| 1580 |  |  |  |  | 1585 |  |  |  |  | 1590 |  |  |  |  |

| Ser | Asn | Arg | Ser | Glu | Ser | Leu | Lys | Lys | Arg | Trp | Ser | Ser | Pro | Tyr |
| 1595 |  |  |  |  | 1600 |  |  |  |  | 1605 |  |  |  |  |

| Ala | Gln | Ile | Ser | Pro | Glu | Asp | Ala | Lys | Lys | Leu | Gly | Ile | Gln | Asp |
| 1610 |  |  |  |  | 1615 |  |  |  |  | 1620 |  |  |  |  |

| Gly | Glu | Met | Ile | Arg | Ile | Val | Thr | Arg | Arg | Gly | Ser | Tyr | Thr | Cys |
| 1625 |  |  |  |  | 1630 |  |  |  |  | 1635 |  |  |  |  |

| Arg | Ala | Val | Val | Thr | Glu | Asp | Val | Ser | Glu | Gly | Val | Ile | Ala | Val |
| 1640 |  |  |  |  | 1645 |  |  |  |  | 1650 |  |  |  |  |

| Pro | Trp | His | Trp | Gly | Ala | Asn | Ile | Leu | Thr | Asn | Asp | Val | Leu | Asp |
| 1655 |  |  |  |  | 1660 |  |  |  |  | 1665 |  |  |  |  |

| Pro | Glu | Ala | Lys | Ile | Pro | Glu | Leu | Lys | Val | Ala | Ala | Cys | Arg | Val |
| 1670 |  |  |  |  | 1675 |  |  |  |  | 1680 |  |  |  |  |

| Glu | Lys | Ile | Gly | Gly | Cys |
| 1685 |  |  |  |  |  |

<210> SEQ ID NO 16
<211> LENGTH: 5076
<212> TYPE: DNA
<213> ORGANISM: Artificial Sequence
<220> FEATURE:
<223> OTHER INFORMATION: Noble Carbon Monoxide:Formate Oxidoreductase

<400> SEQUENCE: 16

| atggccggaa agaaggttcc ctcaaagcaa gtctccataa ctccaggtgt tggaaagctt | 60 |
| attgagaaag ccgaggagga tggggtcaag actgcctggc acagattttt ggagcagcag | 120 |
| cctcagtgtg gattcggtct cttaggtgtc tgctgtaaga actgtacaat gggaccatgt | 180 |
| agaatcgatc cgtttggggt tggcccaact aagggagttt gtggtgcgga tgcagataca | 240 |
| atagtagcaa ggaacattgt aagaatgata gcggctggta ctgccggtca cagcgatcac | 300 |
| tcaagagatg tagtccatgt attcaagggc attgctgaag aaagttcaa ggactataaa | 360 |
| ctaacagatg ttgaaaagct caaagagctg gctaagattc tgggtgtcga aacagagggc | 420 |
| aagagcgaaa atgaaattgc attggaagtc gcccacattc ttgagatgga gttcggaaaa | 480 |
| caggatgagg agccagtaag attacttgca gcaacagcac caaagaagag gattaaggtc | 540 |
| tgggagaagc taggagtctt accaagagcc atcgacaggg agatatgtct cagtatgcac | 600 |
| agaaccccaca taggctgtga tgcagaccct gcaagccttc tactgcatgg tgtgaggact | 660 |
| gccctggccg acggctggtg cggctcaatg atggccactt atctgagcga cattctcttt | 720 |
| ggaacaccaa agccgataaa gtcgctggcg aacctgggag tcttgaagga agacatggtc | 780 |
| aacataatcg ttcacggcca caaccccgatt ctctccatga aaatagcaga gattgcccag | 840 |
| agtgaagaga tgcagaagct tgcagagcag tacggagcaa agggaattaa cgttgctgga | 900 |
| atgtgctgta ccggaaacga agttctctca agaatgggag ttcaggtcgc tggaaacttc | 960 |

```
ctaatgcaag agctggcgat ataactggt gcagttgagg ccgtgatagt tgactaccag    1020
tgcctaatgc cctcattagt tgatgtcgct tcatgttacc acactaagat aataactact    1080
gagccaaagg ctcgcattcc gggagcaata cacgtcgaat ttgaacctga gaaagcggac    1140
gagatcgcca aagagatcat caagattgca attgagaact ataagaacag agttccggca    1200
aaagtctaca ttccagagca caagatggaa ttggttgctg gatttagtgt cgaggcaata    1260
cttgaagccc ttggtggaac actggagccc ctcataaaag ccctccagga cggaacaata    1320
aagggaatcg tcggaatcgt tggatgtaac aatccaaggg tcaagcagaa ctacggtcac    1380
gtcaccttgg ccaaggagct catcaagagg gacatcctgg ttgttggaac tggttgctgg    1440
ggaattgctg cagcaatgca tggattacta accccccgaag cagctgaaat ggccggtcca    1500
gggctgaagg cagtatgcga agcgctcgga attccaccat gcctgcacat gggaagctgt    1560
gttgactgtt cgagaatcct gctggtcttg agtgcccttg ccaatgctct gaatgttgac    1620
atttcagact tgccagttgc tggctctgct ccagaatgga tgagcgagaa ggcagtggca    1680
ataggaacct acttcgttgc aagcggcgtc ttcacgcact gggagttat cccaccagtc    1740 cttggaagcc agaaggttac caaactcctt acggatgaca tcgaggatct ccttggaggg    1800
aagttctacg ttgagacaga tccagtgaaa gcggcagaaa caatatacaa cgtgataatt    1860
gagaagagga aaaaacttgg atggcccatc taaatggaga aaaagctgtt cataaacctc    1920
gggcgctgca ttgcctgccg cgcctgcgag gtggcctgtg agaaggagca cggaatttca    1980
ttcatcacgg tctatgagtt cagggacata gcggttcccc tcaactgccg ccactgtgag    2040
aaggctccgt gtatcgaagt ctgcccgacg aaggccatct atcgcgacga agatggcgca    2100
gttgtgatag acgagtccaa gtgtatcggc tgctacatgt gttcggccgt ctgcccctac    2160
gcgattccga tagttgaccc gataaaggag ctggctgtga agtgtgacct atgtgccgaa    2220
agaaggaagg agggcagaga tccgctctgc gctgcggtct gtcccaccga tgcgataatc    2280
tacgctgacc tcaacgagct gatggaagag aagaggaggc gcaaggccga cgcatcgtc    2340 gaagcccaga ggaaggcggt cgaaacgctc gcctacttcg ggggcggcgg aggcagccca    2400 gcttttccg gttccaacat ggagaagctt acaatttaca taaatccaga gagatgcacg    2460
gggtgcaggg cctgcgaaat tgcctgtgca gttgaacatt caatgagcaa aaacctcttt    2520
ggcgcaattt ttgaaaaacc aaccccccaaa ccccgactcc aagttgttgt cgccgacttc    2580
tttaatgttc caatgagatg ccagcactgt gaggacgctc cctgtatgga ggcctgccca    2640
acaggagcga tctcaaggac caaagaaggc tttgttgtcc ttaacgccaa caagtgcata    2700
ggctgtctca tgtgtgtgat ggcctgtcca tttggccatc ccaagttcga gcccgaatac    2760
aaggctgtga taaaatgcga cagttgtgtt gatagggtca gagaaggcaa agagccagca    2820
tgtgtcgagg cctgtccaac tagagccctg aagttcggga ctctcggcga aatactggaa    2880
gaggttagaa aggagaaggc agagagtctc atatctgggc tgaaatcgca ggggatggtc    2940
tacatgaagc ccgtctccga gtcaaagaag aaagaggatc ttgttagacc tatggatctg    3000
tatcttgcct attcaaatgt agtgtggtat tgaatggagg agtttaagat tggcctgtgc    3060
ccatactgtg gatggggtg caggtttac ataaagactc ttaacgggca gcccatagga    3120
atagagccgt atcccggtgg tgttaatgaa ggaaagctct gtccaaaggg tgtcgccgcc    3180
gttgacttcc tcagacacaa agataggctg aaaaagccgc tcaagagaac tgaaaacggc    3240
ttcgtcgaga taagctggga acaggcgata aaggagattc tgaaaagct tctggagata    3300 cgcgagaagt acgggccgga tacgttaggc ttcttctcaa gtgcccgttg ttccaacgag    3360
```

```
gagaactacc tcctgcagaa aatagcccgc cttctgggca ccaacaacgt cgaccactgc    3420
gcgaggctct gtcacgcctc aacggtcgtc ggtcttgctc agacggttgg cgctgccgct    3480
cagagcggct cctacacgga catacccaag gctaaggtac tcctgatatg gggatacaac    3540
ccgtcagaaa cccacccggt tctcatgcgc tacatcctcc gcgcgaggga caacggggcc    3600
aagataatcg tcgtagatcc gaggaagacg aggactgtct ggttcgccga tatgcacctc    3660
cagcttaagc ctggaacgga catagtccta gccaacgcca tgatgcacgt catcattgaa    3720
gaaaggctct atgacaggga gttcatcatg aaccggacga agggctttga agctcata     3780 gcagctgtcc agaagtacac gccagaatac gccgaggaaa taaccggtgt tcccgccaag    3840
ctcatcagag aagccgctat aacctttgct actgccggac ggggcatcgt gatgtgggca    3900
atgggactga cgcagcacgt cactggggcg ccaacgttaa aggccctcgc tgatctggct    3960
ctgatctgtg gctacgtcgg aagagaagga acaggtctct tcccgatgcg cggtcagaac    4020
aatgttcagg gagcatgtga catggcagcc ttgccaaacg tctttccagg ctatcagaag    4080
gtaactgacg acgagaagag gaagcacgtg gcggaaattt ggggcgttga agatctgccc    4140
tcgaagccgg gccttactat tccagagatg attgatgcgg ctgctaaagg cgagttgaag    4200
gcactctaca taatgggcga gaatccggtc atgagcgatc cgaacacgaa gcacgttatc    4260
gaggctctca agaacctcga acttctcgtt gttcaggata tattcctcac cgaaacggcc    4320
gagctggctc actacgtgct cccagcagcc gcatacgccg agaaggaagg atcattcacc    4380
gcgagcgaga ggcgcgtcca gtggaacttc aaggcgattg agccgccagg agaagccaaa    4440
ccggactggg agatactgac gatgcttgga aaggctctcg gcctgccaaa gttcgactac    4500
tcagacgttg aagatattac gagggagata accctcgttg ctccgcagta ccgtgggata    4560
acccccgaga ggctcaagcg agaggttatg ggtgtgcagt ggccgtgccc gagcgaggat    4620
catcctggaa cgccgaggct gcacgtcgag cgcttcgcca cccccgacgg aaaggccaac    4680
ataatccccg tagagttcaa gccacctgca gaagagcccg atgaggagta cccattcata    4740
ctgacgacat tccgcatcgt cggccagtac cacacactca cgatgagtaa caggagtgaa    4800
agcttgaaga agcgctggtc cagcccgtac gcccagataa gtccggaaga tgcaaagaag    4860
ctgggtatac aggatggtga aatgataagg atagttacga gacgtggaag ctacacctgc    4920
agggcggtcg ttactgaaga tgtctcggaa ggggtgatcg cagttccgtg gcactggggg    4980
gccaatatac tcacgaacga tgtcctcgat ccagaagcaa agattcccga gctgaaggtg    5040
gccgcatgta gggtggagaa gattgggggg tgctga                             5076
```

<210> SEQ ID NO 17
<211> LENGTH: 1140
<212> TYPE: DNA
<213> ORGANISM: Artificial Sequence
<220> FEATURE:
<223> OTHER INFORMATION: Fe-S Fusion Protein

<400> SEQUENCE: 17

```
atggagaaaa agctgttcat aaacctcggg cgctgcattg cctgccgcgc ctgcgaggtg      60
gcctgtgaga aggagcacgg aatttcattc atcacggtct atgagttcag ggacatagcg     120
gttcccctca actgccgcca ctgtgagaag gctccgtgta tcgaagtctg cccgacgaag     180
gccatctatc gcgacgaaga tgcgcagttg tgatagacg agtccaagtg tatcggctgc     240
tacatgtgtt cggccgtctg cccctacgcg attccgatag ttgacccgat aaaggagctg     300
```

```
gctgtgaagt gtgacctatg tgccgaaaga aggaaggagg gcagagatcc gctctgcgct    360
gcggtctgtc ccaccgatgc gataatctac gctgacctca acgagctgat ggaagagaag    420
aggaggcgca aggccgagcg catcgtcgaa gcccagagga aggcggtcga aacgctcgcc    480
tacttcgggg gcggcggagg cagcccagct ttttccggtt ccaacatgga gaagcttaca    540
atttacataa atccagagag atgcacgggg tgcagggcct gcgaaattgc ctgtgcagtt    600
gaacattcaa tgagcaaaaa cctctttggc gcaattttg aaaaaccaac ccccaaaccc     660
cgactccaag ttgttgtcgc cgacttcttt aatgttccaa tgagatgcca gcactgtgag    720
gacgctccct gtatggaggc ctgcccaaca ggagcgatct caaggaccaa agaaggcttt    780
gttgtcctta acgccaacaa gtgcataggc tgtctcatgt gtgtgatggc ctgtccattt    840
ggccatccca gttcgagcc cgaatacaag gctgtgataa aatgcgacag ttgtgttgat     900
agggtcagag aaggcaaaga gccagcatgt gtcgaggcct gtccaactag agccctgaag    960
ttcgggactc tcggcgaaat actggaagag gttagaaagg agaaggcaga gagtctcata   1020
tctgggctga aatcgcaggg gatggtctac atgaagcccg tctccgagtc aaagaagaaa   1080
gaggatcttg ttagacctat ggatctgtat cttgcctatt caaatgtagt gtggtattga   1140
```

<210> SEQ ID NO 18
<211> LENGTH: 47
<212> TYPE: DNA
<213> ORGANISM: Artificial Sequence
<220> FEATURE:
<223> OTHER INFORMATION: Forward primer used for PCR of fdh3 of BCF01,
      BCF02, BCF03 or BCF12

<400> SEQUENCE: 18

```
taaaatgctt gggagatgac ctaggatggc acagaataat tcactcg                   47
```

<210> SEQ ID NO 19
<211> LENGTH: 42
<212> TYPE: DNA
<213> ORGANISM: Artificial Sequence
<220> FEATURE:
<223> OTHER INFORMATION: Linker-containing reverse primer used for PCR
      of fdh3 of BCF01

<400> SEQUENCE: 19

```
ggcatgctgc ctccgccgcc ccccaggtaa gcctcatatt tg                        42
```

<210> SEQ ID NO 20
<211> LENGTH: 52
<212> TYPE: DNA
<213> ORGANISM: Artificial Sequence
<220> FEATURE:
<223> OTHER INFORMATION: Linker-containing reverse primer used for PCR
      of fdh3 of BCF02

<400> SEQUENCE: 20

```
gctgcctccg ccgccgcttc cgcctcctcc ccccaggtaa gcctcatatt tg             52
```

<210> SEQ ID NO 21
<211> LENGTH: 37
<212> TYPE: DNA
<213> ORGANISM: Artificial Sequence
<220> FEATURE:
<223> OTHER INFORMATION: Linker-containing reverse primer used for PCR
      of fdh3 of BCF12

<400> SEQUENCE: 21

```
gctgggctgc ctccgccgcc cccgaagtag gcgagcg                              37
```

<210> SEQ ID NO 22
<211> LENGTH: 40
<212> TYPE: DNA
<213> ORGANISM: Artificial Sequence
<220> FEATURE:
<223> OTHER INFORMATION: Linker-containing forward primer used for PCR
      of codh of BCF01

<400> SEQUENCE: 22 tgggggggcgg cggaggcagc atgccagctt tttccggttc                         40

<210> SEQ ID NO 23
<211> LENGTH: 50
<212> TYPE: DNA
<213> ORGANISM: Artificial Sequence
<220> FEATURE:
<223> OTHER INFORMATION: Linker-containing forward primer used for PCR
      of codh of BCF02

<400> SEQUENCE: 23
ggcggcggag gcagcggagg aggcggaagc atgccagctt tttccggttc               50

<210> SEQ ID NO 24
<211> LENGTH: 38
<212> TYPE: DNA
<213> ORGANISM: Artificial Sequence
<220> FEATURE:
<223> OTHER INFORMATION: Linker-containing forward primer used for PCR
      of codh of BCF12

<400> SEQUENCE: 24
tcgggggcgg cggaggcagc ccagcttttt ccggttcc                            38

<210> SEQ ID NO 25
<211> LENGTH: 55
<212> TYPE: DNA
<213> ORGANISM: Artificial Sequence
<220> FEATURE:
<223> OTHER INFORMATION: Reverse primer used for PCR of codh of BCF01,
      BCF02, BCF03 or BCF12

<400> SEQUENCE: 25
tggccatcgt tgacgccacg catgcgacgt ctcacctcct gagtttaaac ctcat         55

<210> SEQ ID NO 26
<211> LENGTH: 41
<212> TYPE: DNA
<213> ORGANISM: Artificial Sequence
<220> FEATURE:
<223> OTHER INFORMATION: Left arm (LA) reverse primer used for insert
      DNA PCR of BCF09 and containing his-tag at N-terminus of Fdh3

<400> SEQUENCE: 26
tcctcgtgat ggtggtgatg gtgcatccgc accaccgccc t                        41

<210> SEQ ID NO 27
<211> LENGTH: 44
<212> TYPE: DNA
<213> ORGANISM: Artificial Sequence
<220> FEATURE:
<223> OTHER INFORMATION: Right arm (RA) reverse primer used for insert
      DNA PCR of BCF09 and containing his-tag at N-terminus of Fdh3

<400> SEQUENCE: 27
ggatgcacca tcaccaccat cacgaggagt ttaagattgg cctg                     44

<210> SEQ ID NO 28
<211> LENGTH: 41
<212> TYPE: DNA
<213> ORGANISM: Artificial Sequence
<220> FEATURE:
<223> OTHER INFORMATION: Left arm (LA) reverse primer containing his-tag
at C-terminus of Fdh3

<400> SEQUENCE: 28
cttcagtgat ggtggtgatg gtggcacccc ccaatcttct c        41

<210> SEQ ID NO 29
<211> LENGTH: 46
<212> TYPE: DNA
<213> ORGANISM: Artificial Sequence
<220> FEATURE:
<223> OTHER INFORMATION: Right arm (RA) reverse primer containing
his-tag at C-terminus of Fdh3

<400> SEQUENCE: 29
ggtgccacca tcaccaccat cactgaagat ggagaaaaag ctgttc        46

<210> SEQ ID NO 30
<211> LENGTH: 46
<212> TYPE: DNA
<213> ORGANISM: Artificial Sequence
<220> FEATURE:
<223> OTHER INFORMATION: Left arm (LA) reverse primer containing his-tag
at N-terminus of Codh

<400> SEQUENCE: 30
ccggcgtgat ggtggtgatg gtgcattttc accacctcaa taccac        46

<210> SEQ ID NO 31
<211> LENGTH: 41
<212> TYPE: DNA
<213> ORGANISM: Artificial Sequence
<220> FEATURE:
<223> OTHER INFORMATION: Right arm (RA) reverse primer containing
his-tag at N-terminus of Codh

<400> SEQUENCE: 31
aaatgcacca tcaccaccat cacgccggaa agaaggttcc c        41

<210> SEQ ID NO 32
<211> LENGTH: 45
<212> TYPE: DNA
<213> ORGANISM: Artificial Sequence
<220> FEATURE:
<223> OTHER INFORMATION: Left arm (LA) reverse primer used for insert
DNA PCR of BCF07 and containing his-tag at C-terminus of Codh

<400> SEQUENCE: 32
tattagtgat ggtggtgatg gtggatgggc catccaagtt ttttc        45

<210> SEQ ID NO 33
<211> LENGTH: 49
<212> TYPE: DNA
<213> ORGANISM: Artificial Sequence
<220> FEATURE:
<223> OTHER INFORMATION: Right (RA) reverse primer used for insert DNA
PCR of BCF07 and containing his-tag at C-terminus of Codh

<400> SEQUENCE: 33
ccatccacca tcaccaccat cactaatagt ttctattatt ttaactttg        49